United States Patent
Lee et al.

(10) Patent No.: US 10,301,628 B2
(45) Date of Patent: May 28, 2019

(54) TREATMENT OF IDIOPATHIC PULMONARY FIBROSIS USING RNA COMPLEXES THAT TARGET CONNECTIVE TISSUE GROWTH FACTOR

(71) Applicant: OliX Pharmaceuticals, Inc., Seoul (KR)

(72) Inventors: Dong Ki Lee, Seoul (KR); Sun Woo Hong, Seoul (KR); Tae Yeon Lee, Seoul (KR); Sae-Lo-Oom Lee, Seoul (KR); Ji Hyun Kim, Seoul (KR); Yu Ran Na, Gyeonggi-do (KR); Young-Dong Kim, Seoul (KR)

(73) Assignee: OliX Pharmaceuticals, Inc., Seoul (KR)

( * ) Notice: Subject to any disclaimer, the term of this patent is extended or adjusted under 35 U.S.C. 154(b) by 0 days.

(21) Appl. No.: 15/483,305

(22) Filed: Apr. 10, 2017

(65) Prior Publication Data

US 2017/0298358 A1   Oct. 19, 2017

Related U.S. Application Data

(60) Provisional application No. 62/320,944, filed on Apr. 11, 2016.

(51) Int. Cl.
*C12N 15/113*     (2010.01)
*A61K 9/00*       (2006.01)

(52) U.S. Cl.
CPC .......... *C12N 15/1136* (2013.01); *A61K 9/007* (2013.01); *C12N 2310/14* (2013.01); *C12N 2310/315* (2013.01); *C12N 2310/321* (2013.01); *C12N 2310/3515* (2013.01); *C12N 2310/50* (2013.01)

(58) Field of Classification Search
CPC .......... C12N 15/113; C12N 15/1136
See application file for complete search history.

(56) References Cited

U.S. PATENT DOCUMENTS

| | | | |
|---|---|---|---|
| 10,125,362 B2 * | 11/2018 | Hong | .......... C12N 15/113 |
| 2006/0160123 A1 | 7/2006 | Quay | |
| 2011/0028534 A1 | 2/2011 | Shepard et al. | |
| 2012/0238017 A1 | 9/2012 | Lee et al. | |
| 2015/0111948 A1 | 4/2015 | Hong | |

FOREIGN PATENT DOCUMENTS

| | | | |
|---|---|---|---|
| WO | WO-2011119887 A1 | 9/2011 | |
| WO | WO-2013176477 A1 * | 11/2013 | .......... C12N 15/113 |
| WO | WO-2015002513 A2 | 1/2015 | |

OTHER PUBLICATIONS

International Search Report and Written Opinion for International Application No. PCT/IB2017/000470 dated Jul. 24, 2017.

* cited by examiner

*Primary Examiner* — J. E. Angell
(74) *Attorney, Agent, or Firm* — Morgan, Lewis & Bockius, LLP

(57) ABSTRACT

In certain aspects, provided herein are RNA complexes (e.g., asymmetric RNA complexes, such as asiRNAs or cell penetrating asiRNAs) that inhibit CTGF expression and are therefore useful for treating idiopathic pulmonary fibrosis.

12 Claims, 15 Drawing Sheets
Specification includes a Sequence Listing.

TREATMENT OF IDIOPATHIC PULMONARY FIBROSIS USING RNA COMPLEXES THAT TARGET CONNECTIVE TISSUE GROWTH FACTOR

RELATED APPLICATIONS

This application claims the benefit of priority to U.S. Provisional Application No. 62/320,944, filed Apr. 11, 2016, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 14, 2017, is named OPH-00901_SL.txt and is 65,652 bytes in size.

BACKGROUND

Idiopathic pulmonary fibrosis (IPF) is characterized by severe and progressive scarring (fibrosis) of lung tissue. Many people live only about 3 to 5 years after diagnosis, and death is mainly due to respiratory failure. Approximately 70,000 patients in the United States and the European Union suffer from IPF. No effective cure exists except lung transplantation, for which less than 1% of patients qualify. Hence, there remains a significant need for new, clinically efficacious IPF therapeutics which can effectively inhibit or reduce lung fibrosis in patients.

Several growth factors are implicated in the pathogenesis of IPF. Of these growth factors, Connective Tissue Growth Factor (CTGF) appears to be implicated in the transformation of multiple cell types into myofibroblasts and impairs important antifibrotic and proregenerative repair factors. CTGF levels are elevated in plasma, in transbronchial biopsy specimens, and in bronchoalveolar lavage fluid of IPF patients.

Thus, there is a need for new and improved therapeutics targeting CTGF for the treatment of idiopathic pulmonary fibrosis.

SUMMARY

In certain aspects, provided herein are RNA complexes that target CTGF and are useful for treating and/or preventing idiopathic pulmonary fibrosis (IPF). In certain aspects, provided herein are pharmaceutical compositions comprising such RNA complexes and methods of using such RNA complexes and pharmaceutical compositions.

In certain aspects, provided herein is an RNA complex comprising an antisense strand having sequence complementarity to a CTGF mRNA sequence and a sense strand having sequence complementarity to the antisense strand. In some embodiments, the RNA complex is capable of inhibiting CTGF expression by a cell (e.g., an alveolar cell, an epithelial cell, an Hs68, an HaCaT, or an A549 cell). In some embodiments, the RNA complex is an asymmetric short interfering RNA (an asiRNA). In some embodiments, the RNA complex is a cell penetrating asymmetric short interfering RNA (a cp-asiRNA). In some embodiments, the RNA complex is an RNA complex listed in Table 1, Table 2, Table 3, or Table 6.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a hydrophobic moiety. In some embodiments, the RNA complexes provided herein comprise a hydrophobic moiety. In some embodiments, the hydrophobic moiety can be any chemical structure having hydrophobic character. For example, in some embodiments the hydrophobic moiety is a lipid, a lipophilic peptide and/or a lipophilic protein. In some embodiments, the hydrophobic moiety is a lipid, such as cholesterol, tocopherol, or a long-chain fatty acid having 10 or more carbon atoms (e.g., stearic acid or palmitic acid). In some embodiments, the hydrophobic moiety is cholesterol. In some embodiments, the RNA complex is a modified RNA complex listed in Table 2, Table 3, or Table 6. In certain embodiments, the RNA complex is not cytotoxic.

In certain aspects, provided herein is a pharmaceutical composition comprising an RNA complex as described and a pharmaceutically acceptable carrier. In some embodiments, the pharmaceutical composition is formulated for parenteral, intravenous, or oral delivery. In other embodiments, the pharmaceutical composition is formulated for inhalation.

In certain aspects, provided herein is a method of inhibiting CTGF expression by a cell (e.g., an alveolar cell, an epithelial cell, an Hs68, an HaCaT, or an A549 cell), comprising contacting the cell with an RNA complex as described herein.

In certain aspects, as described herein is a method of inhibiting gene expression CTGF in a human subject comprising administering to the subject an RNA complex or pharmaceutical composition provided herein. In certain aspects, provided herein is a method of treating a human subject for IPF comprising administering to the subject an RNA complex or pharmaceutical composition as described herein.

DETAILED DESCRIPTION

General

Figure 1:
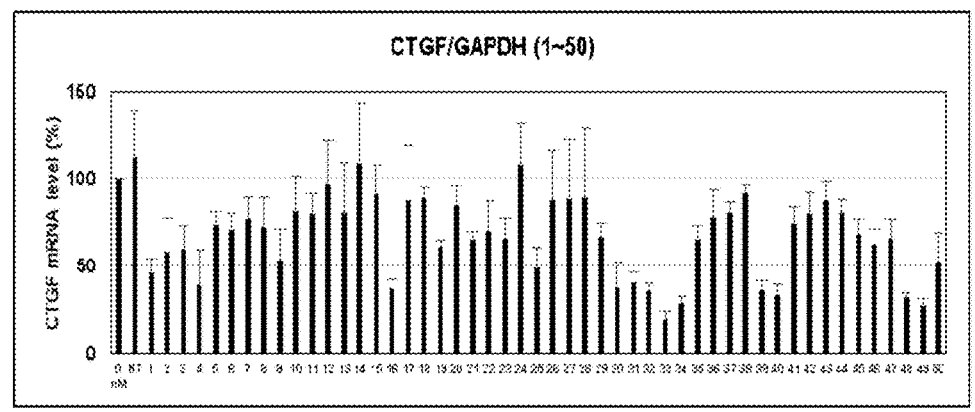
FIG. 1 shows the gene silencing efficiency of 100 exemplary asiRNAs that target CTGF.
Figure 1:
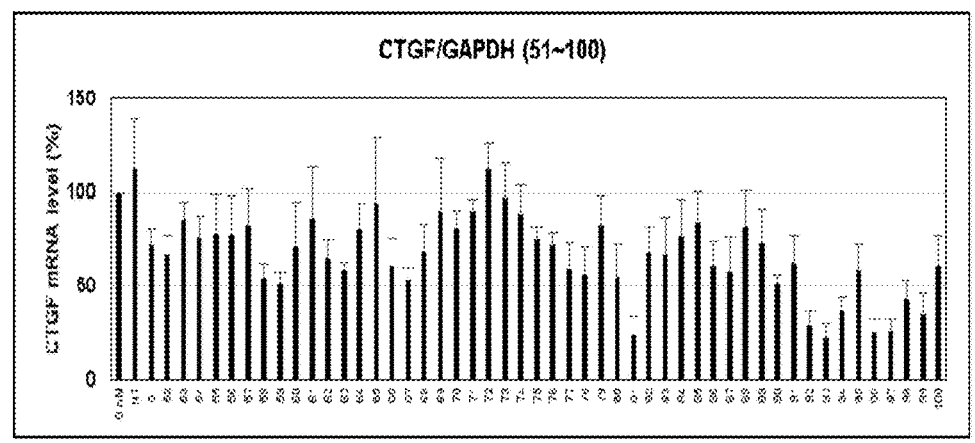

In certain aspects, provided herein are asymmetric RNA complexes (e.g., asiRNAs or cp-asiRNAs) that inhibit CTGF and are therefore useful for the treatment of IPF. In some embodiments, the RNA complexes are chemically modified to be capable of penetrating a cell without need for a transfection vehicle. In some embodiments, the RNA complex is an RNA complex listed in Table 1, Table 2, Table 3, or Table 6. In certain aspects, provided herein are pharmaceutical compositions comprising such RNA complexes and methods of using such RNA complexes and pharmaceutical compositions.

In some embodiments, the RNA complexes described herein are asiRNAs or cp-siRNAs. As used herein, the term asiRNA refers to double-stranded asymmetrical short interfering RNA molecules that have a 19-21 nt antisense strand and a 13-17 nt sense strand. Additional information on asiRNAs can be found in U.S. Pat. Pub. No. 2012/0238017 and in Chang et al., Mol. Ther. 17:725-732 (2009), each of which is hereby incorporated by reference in its entirety.

In some embodiments, the RNA complexes described herein are delivered to cells using a delivery vehicle, such as liposomes, cationic polymers, cell penetrating peptides (CPPs), protein transduction domains (PTDs), antibodies and/or aptamers. In some embodiments, the RNA complex described herein is chemically modified so as to not require the use of such delivery vehicles to mediate CTGF inhibition in a cell. Such RNA complexes are referred to herein as cell-penetrating asiRNAs (cp-asiRNAs).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, the terms "interfering nucleic acid" and "inhibiting nucleic acid" are used interchangeably. Interfering nucleic acids generally include a sequence of cyclic subunits, each bearing a base-pairing moiety, linked by intersubunit linkages that allow the base-pairing moieties to hybridize to a target sequence in a nucleic acid (typically RNA) by Watson-Crick base pairing, to form a nucleic acid: oligomer heteroduplex within the target sequence. Interfering RNA molecules include, but are not limited to, antisense molecules, siRNA molecules, asiRNA molecules, cp-asiRNA molecules, single-stranded siRNA molecules, miRNA molecules and shRNA molecules. Such an interfering nucleic acids can be designed to block or inhibit translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a heteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "polynucleotide", and "nucleic acid" are used interchangeably. They refer to a polymeric form of nucleotides, whether deoxyribonucleotides, ribonucleotides, or analogs thereof, in any combination and of any length. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleobases are interchangeable with T nucleobases.

The phrase "pharmaceutically-acceptable carrier" as used herein means a pharmaceutically-acceptable material, composition or vehicle, such as a liquid or solid filler, diluent, excipient, or solvent encapsulating material.

An oligonucleotide "specifically hybridizes" to a target polynucleotide if the oligomer hybridizes to the target under physiological conditions, with a Tm substantially greater than 45° C., or at least 50° C., or at least 60° C.–80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

RNA Complexes

In certain aspects, provided herein are RNA complexes that target CTGF mRNA and inhibit CTGF expression by a cell, respectively. The nucleic acid sequence of human CTGF cDNA is provided below.

```
Human CTGF mRNA. (NM_001901.2)
Homo sapiens connective tissue growth factor (CTGF), mRNA
   1  aaactcacac aacaactctt ccccgctgag aggagacagc cagtgcgact ccaccctcca 61  gctcgacggc agccgcccg gccgacagcc ccgagacgac agcccggcgc gtcccggtcc 121  ccacctccga ccaccgccag cgctccaggc cccgccgctc cccgctcgcc gccaccgcgc 181  cctccgctcc gcccgcagtg ccaaccatga ccgccgccag tatgggcccc gtccgcgtcg 241  ccttcgtggt cctcctcgcc ctctgcagcc ggccggccgt cggccagaac tgcagcgggc 301  cgtgccggtg cccggacgag ccggcgccgc gctgcccggc gggcgtgagc ctcgtgctgg 361  acggctgcgg ctgctgccgc gtctgcgcca agcagctggg cgagctgtgc accgagcgcg 421  accccctgcga cccgcacaag ggcctcttct gtgacttcgg ctccccggcc aaccgcaaga 481  tcggcgtgtg caccgccaaa gatggtgctc cctgcatctt cggtggtacg gtgtaccgca 541  gcggagagtc cttccagagc agctgcaagt accagtgcac gtgcctggac ggggcggtgg 601  gctgcatgcc cctgtgcagc atggacgttc gtctgccag ccctgactgc cccttcccga 661  ggagggtcaa gctgcccggg aaatgctgcg aggagtgggt gtgtgacgag cccaaggacc 721  aaaccgtggt tgggcctgcc ctcgcggctt accgactgga agacacgttt ggcccagacc 781  caactatgat tagagccaac tgcctggtcc agaccacaga gtggagcgcc tgttccaaga 841  cctgtgggat gggcatctcc acccgggtta ccaatgacaa cgcctcctgc aggctagaga 901  agcagagccg cctgtgcatg gtcaggcctt gcgaagctga cctggaagag aacattaaga 961  agggcaaaaa gtgcatccgt actcccaaaa tctccaagcc tatcaagttt gagctttctg 1021  gctgcaccag catgaagaca taccgagcta aattctgtgg agtatgtacc gacggccgat 1081  gctgcacccc ccacagaacc accaccctgc cggtggagtt caagtgccct gacggcgagg 1141  tcatgaagaa gaacatgatg ttcatcaaga cctgtgcctg ccattacaac tgtcccggag 1201  acaatgacat ctttgaatcg ctgtactaca ggaagatgta cggagacatg catgaagcc 1261  agagagtgag agacattaac tcattagact ggaacttgaa ctgattcaca tctcattttt 1321  ccgtaaaaat gatttcagta gcacaagtta tttaaatctg ttttcctaac tgggggaaaa 1381  gattcccacc caattcaaaa cattgtgcca tgtcaaacaa atagtctatc aacccagac 1441  actggtttga agaatgttaa gacttgacag tggaactaca ttagtacaca gcaccagaat 1501  gtatattaag gtgtggcttt aggagcagtg ggagggtacc agcagaaagg ttagtatcat 1561  cagatagcat cttatacgag taatatgcct gctatttgaa gtgtaattga aaggaaaat 1621  tttagcgtgc tcactgacct gcctgtagcc ccagtgacag ctaggatgtg cattctccag 1681  ccatcaagag actgagtcaa gttgttcctt aagtcagaac agcagactca gctctgacat 1741  tctgattcga atgacactgt tcaggaatcg gaatcctgtc gattagactg gacagcttgt 1801  ggcaagtgaa tttgcctgta acaagccaga ttttttaaaa tttatattgt aaatattgtg 1861  tgtgtgtgtg tgtgtgtata tatatatata tgtacagtta tctaagttaa tttaaagttg 1921  tttgtgcctt tttattttttg tttttaatgc tttgatattt caatgttagc ctcaatttct 1981  gaacaccata ggtagaatgt aaagcttgtc tgatcgttca aagcatgaaa tggatactta 2041  tatggaaatt ctgctcagat agaatgacag tccgtcaaaa cagattgttt gcaaagggga 2101  ggcatcagtg tccttggcag gctgatttct aggtaggaaa tgtggtagcc tcacttttaa
```

```
                            -continued
2161    tgaacaaatg gcctttatta aaaactgagt gactctatat agctgatcag tttttcacc 2221    tggaagcatt tgtttctact ttgatatgac tgtttttcgg acagtttatt tgttgagagt 2281    gtgaccaaaa gttacatgtt tgcacctttc tagttgaaaa taaagtgtat atttttcta 2341    taaaaaaaaa aaaaaaaa (SEQ ID NO: 45)
```

In certain aspects, provided herein is an RNA complex comprising an antisense strand having sequence complementarity to an CTGF mRNA sequence (e.g., a human CTGF mRNA sequence) and a sense strand having sequence complementarity to the antisense strand. In some embodiments, the RNA complex is capable of inhibiting CTGF expression by a cell (e.g., an alveolar cell, an epithelial cell, an Hs68, an HaCaT, or an A549 cell). In some embodiments, the RNA complex is an asymmetric short interfering RNA (an asiRNA). In some embodiments, the RNA complex is an RNA complex listed in Table 1, Table 2, Table 3, or Table 6. The RNA complexes described herein can contain RNA bases, non-RNA bases or a mixture of RNA bases and non-RNA bases. For example, certain RNA complexes provided herein can be primarily composed of RNA bases but also contain DNA bases or non-naturally occurring nucleotides.

In some embodiments, the antisense strand is at least 19 nucleotides (nt) in length. In some embodiments, the antisense strand is 19 to 21 nt in length (i.e., 19, 20 or 21 nt in length). In some embodiments, the antisense strand is at least 21 nucleotides (nt) in length.

In some embodiments, the antisense strand is 21 to 31 nt in length (i.e., 21, 22, 23, 24, 25, 26, 27, 28, 29, 30, or 31 nt in length). In some embodiments, at least 13, 14, 15, 16, 17, 18, 19, 20, 21, 22, 23, 24, 25, 26, 27, 28, 29, 30, or 31 nt of the antisense strand are complementary to the CTGF mRNA sequence. Perfect complementarity is not necessary. In some embodiments, the antisense strand is perfectly complementary to the CTGF mRNA sequence.

In some embodiments, the antisense strand is at least 24 nt in length (e.g., at least 25 nt in length, at least 26 nt in length, at least 27 nt in length, at least 28 nt in length, at least 29 nt in length, at least 30 nt in length or at least 31 nt in length). In some embodiments, the antisense strand is no greater than 124 nt in length (e.g., no greater than 100 nt in length, no greater than 90 nt in length, no greater than 80 nt in length, no greater than 70 nt in length, no greater than 60 nt in length, no greater than 50 nt in length or no greater than 40 nt in length. In some embodiments, the antisense strand is 21 nt in length. In some embodiments, the antisense strand is 23 nt in length. In some embodiments, the antisense strand is 25 nt in length. In some embodiments, the antisense strand is 27 nt in length. In some embodiments, the antisense strand is 29 nt in length. In some embodiments, the antisense strand is 31 nt in length. In some embodiments, at least 16, 17, 18, 19, 20, 21, 22, 23, 24, 25, 26, 27, 29, 29, 30 or 31 nt of the antisense strand are complementary to the CTGF mRNA sequence. Perfect complementarity is not necessary. In some embodiments, the antisense strand is perfectly complementary to the CTGF mRNA sequence.

In some embodiments, the sense strand is 15 to 17 nt in length (i.e., 15 nt in length, 16 nt in length or 17 nt in length). In some embodiments, at least 15 nt, at least 16 nt or at least 17 nt of the sense strand are complementary to the sequence of the antisense strand. In some embodiments the sense strand is perfectly complementary to the sequence of the antisense strand. In some embodiments, the sense strand is 16 nt in length.

In some embodiments, the antisense strand and the sense strand form a complex in which the 5' end of the antisense strand and the 3' end of the sense strand form a blunt end. In some embodiments, the antisense strand and the sense strand form a complex in which the 5' end of the antisense strand overhangs the 3' end of the sense strand (e.g., by 1, 2, 3, 4 or 5 nt). In some embodiments, the antisense strand and the sense strand form a complex in which the 5' end of the sense strand overhangs the 3' end of the antisense strand (e.g., by 1, 2, 3, 4 or 5 nt).

In some embodiments, the antisense strand and/or the sense strand of the RNA complex has a sense strand sequence and/or an antisense strand sequence selected from the sequences listed in Table 1, Table 2, Table 3, or Table 6.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a hydrophobic moiety. In some embodiments, the chemical modification is a hydrophobic moiety. In some embodiments, the hydrophobic moiety is a cholesterol moiety. In some embodiments, the RNA complex is a modified RNA complex listed in Table 2, Table 3, or Table 6. In certain embodiments, the RNA complex is not cytotoxic.

The RNA complexes described herein can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, each of which is hereby incorporated by reference in its entirety.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition. The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE.TM. has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539,082; 5,714,331; and 5,719,262 for the preparation of PNAs. Further teaching of PNA compounds can be found in Nielsen et al., *Science*, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C3-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., *Chemical Communications* (1998) 455; *Tetrahedron* (1998) 54:3607, and *Accounts of Chem. Research* (1999) 32:301); Obika, et al., *Tetrahedron Letters* (1997) 38:8735; (1998) 39:5401, and *Bioorganic Medicinal Chemistry* (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA-containing compound where each LNA subunit is separated by a DNA subunit. Certain compounds are composed of alternating LNA and DNA subunits where the intersubunit linker is phosphorothioate.

In certain embodiments, the RNA complex is linked to a cholesterol moiety. In some embodiments, the cholesterol moiety is attached to the 3' terminus of the sense strand. In some embodiments, the cholesterol moiety is attached to the 3' terminus of the antisense strand. In some embodiments, the cholesterol moiety is attached to the 5' terminus of the sense strand. In some embodiments, the cholesterol moiety is attached to the 5' terminus of the antisense strand.

In some embodiments, the RNA complex comprises a 2'-O-methylated nucleoside. 2'-O-methylated nucleosides carry a methyl group at the 2'-OH residue of the ribose molecule. 2'-O-Me-RNAs show the same (or similar) behavior as RNA, but are protected against nuclease degradation. 2'-O-Me-RNAs can also be combined with phosphothioate oligonucleotides (PTOs) for further stabilization. 2'-O-Me-RNAs (phosphodiester or phosphothioate) can be synthesized according to routine techniques in the art (see, e.g., Yoo et al., *Nucleic Acids Res.* 32:2008-16, 2004, which is hereby incorporated by reference).

In some embodiments, the 2'-O-methyl nucleoside is positioned on the sense strand.

In some embodiments, the 2'-O-methyl nucleoside is positioned at the 3' terminus of the sense strand. In some embodiments, the sense strand comprises a plurality of 2'-O-methylated nucleosides (e.g., 2, 3, 4, 5 or 6 2'-O-methylated nucleosides). In some embodiments, the 2'-O-methyl nucleoside is positioned at the 3' terminus of the antisense strand. In some embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the sense strand and the 3' terminal region of the antisense strand comprise a plurality of 2'-O-methylated nucleosides. In some embodiments, the sense strand comprises 2'-O-methylated nucleosides that alternate with unmodified nucleosides. In some embodiments, the sense strand comprises a contiguous sequence of 2, 3, 4, 5, 6, 7 or 8 2'-O-methylated nucleosides that alternate with unmodified nucleosides. In some embodiments, the anti-sense strand comprises 2'-O-methylated nucleosides that alternate with unmodified nucleosides. In some embodiments, the anti-sense strand comprises a contiguous sequence of 2, 3, 4, 5, 6, 7 or 8 2'-O-methylated nucleosides that alternate with unmodified nucleosides.

In some embodiments, the RNA complex comprises a phosphorothioate bond. "Phosphorothioates" (or S-oligos) are a variant of normal DNA in which one of the non-bridging oxygens is replaced by a sulfur. The sulfurization of the internucleotide bond reduces the action of endo-and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-benzodithiol-3-one 1,1-dioxide (BDTD) (see, e.g., Iyer et al., *J. Org. Chem.* 55, 4693-4699, 1990). The latter methods avoid the problem of elemental sulfur's insolubility in most organic solvents and the toxicity of carbon disulfide. The TETD and BDTD methods also yield higher purity phosphorothioates.

In some embodiments, at least 1%, 5%, 10%, 15%, 20%, 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some embodiments, all of the bonds between the ribonucleotides in the sense strand of the RNA complex are phosphorothioate bonds.

In some embodiments, at least 1%, 5%, 10%, 15%, 20%, 25%, 30%, 35%, 40%, 45%, 50%, 55%, 60%, 65%, 70%, 75%, 80%, 85%, 90% or 95% of the bonds between the ribonucleotides in the antisense strand of the RNA complex are phosphorothioate bonds. In some embodiments, all of the bonds between the ribonucleotides in the antisense strand of the RNA complex are phosphorothioate bonds.

The RNA complexes described herein may be contacted with a cell or administered to an organism (e.g., a human). Alternatively, constructs and/or vectors encoding the RNA complexes may be contacted with or introduced into a cell or organism. In certain embodiments, a viral, retroviral or lentiviral vector is used.

The RNA complexes described herein can be prepared by any appropriate method known in the art. For example, in some embodiments, the RNA complexes described herein are prepared by chemical synthesis or in vitro transcription.

In certain aspects, provided herein is a pharmaceutical composition comprising an RNA complex as disclosed herein and a pharmaceutically acceptable carrier. In certain embodiments, the pharmaceutical composition is formulated for delivery to the lungs (e.g., as an inhaler). In some embodiments, the pharmaceutical composition is formulated for oral or parenteral delivery. In some embodiments, the pharmaceutical composition further comprises a second agent for treatment of IPF. In some embodiments, the second agent is a growth factor inhibitor. Examples of growth factor inhibitors include nintedanib, pirfenidone, gefitinib, erlotinib, lapatinib, cetuximab, pantiumumab, osimertinib, necitumumab, and vandetanib. In some embodiments, the second agent is a steroid. Examples of steroids include hydrocortisone, fluticasone, mudesonide, mometasone, beclomethasone, ciclesonide, flunisolide cortisone, and prednisone. Two or more growth factor inhibitors and/or steroids may be taken in with the pharmaceutical composition.

In certain embodiments, the pharmaceutical composition does not comprise a transfection vehicle. In some embodiments, the pharmaceutical composition comprises a delivery vehicle (e.g., liposomes, cationic polymers, cell penetrating peptides (CPPs), protein transduction domains (PTDs), antibodies and/or aptamers). In some embodiments, the composition includes a combination of multiple (e.g., two or more) of the RNA complexes described herein.

Methods of preparing these formulations or compositions include the step of bringing into association an RNA complex described herein with the carrier and, optionally, one or more accessory ingredients. In general, the formulations are prepared by uniformly and intimately bringing into association an agent described herein with liquid carriers.

Therapeutic Methods

In certain aspects, provided herein is a method of inhibiting CTGF expression by a cell, comprising contacting the cell with an RNA complex as described herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPPs), protein transduction domain (PTDs), antibody and/or aptamer). In some embodiments, the cell is present in the respiratory tract of a human subject. In some embodiments, the subject has IPF. In some embodiments, the subject is female. In some embodiments, the subject is male.

In certain aspects, provided herein is a method of treating a human subject for IPF comprising administering to the subject an RNA complex or pharmaceutical composition as described herein. In certain embodiments, the RNA complex or pharmaceutical composition is administered to the respiratory tract of the subject. In some embodiments, the RNA complex or pharmaceutical composition self-administered by the subject.

In the present methods, an RNA complex described herein can be administered to the subject, for example, as nucleic acid without delivery vehicle (e.g., for cp-asiRNAs), in combination with a delivery reagent, and/or as a nucleic acid comprising sequences that express the RNA complex described herein. In some embodiments, any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. *Nucleic Acids Res.*, 32(13):e109 (2004); Hanai et al. *Ann NY Acad Sci.*, 1082:9-17 (2006); and Kawata et al. *Mol Cancer Ther.*, 7(9):2904-12 (2008); each of which is incorporated herein in their entirety. Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference in its entirety.

In some embodiments of the methods described herein, liposomes are used to deliver an RNA complex described herein to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

The pharmaceutical compositions disclosed herein may be delivered by any suitable route of administration, through inhalation, orally, and parenterally. In certain embodiments the pharmaceutical compositions are delivered systemically (e.g., via oral or parenteral administration). In certain other embodiments the pharmaceutical compositions are delivered locally through inhalation into the lungs.

Actual dosage levels of the RNA complexes in the pharmaceutical compositions may be varied so as to obtain an amount of RNA complex that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an RNA complex described herein will be that amount of the RNA complex which is the lowest dose effective to produce a therapeutic effect. Such an effective dose will generally depend upon the factors described above.

EXEMPLIFICATION

Example 1

Screening for CTGF-specific Asymmetric Small Interfering RNAs

To identify asymmetric small interfering RNAs (asiRNAs) that inhibit connective tissue growth factor (CTGF), 100 asiRNAs were synthesized and screened. The nucleic acid sequences of the exemplary asiRNAs are provided in Table 1.

TABLE 1

Nucleic acid sequences for exemplary CTGF-targeting asiRNA.

| SEQUENCE | SEQ ID NO: |
|---|---|
| 1CTGF S: 5'-CAUAGGUAGAAUGUAA-3' | 46 |
| 1CTGF AS: 5'-UUACAUUCUACCUAUGGUGUU-3' | 47 |
| 2CTGF S: 5'-UAUAGCUGAUCAGUUU-3' | 48 |
| 2CTGF AS: 5'-AAACUGAUCAGCUAUAUAGAG-3' | 49 |
| 3CTGF S: 5'-CCAGCAUGAAGACAUA-3' | 50 |
| 3CTGF AS: 5'-UAUGUCUUCAUGCUGGUGCAG-3' | 51 |
| 4CTGF S: 5'-CCAGAAUGUAUAUUAA-3' | 52 |
| 4CTGF AS: 5'-UUAAUAUACAUUCUGGUGCUG-3' | 53 |
| 5CTGF S: 5'-CAAAUGGCCUUUAUUA-3' | 54 |
| 5CTGF AS: 5'-UAAUAAAGGCCAUUUGUUCAU-3' | 55 |
| 6CTGF S: 5'-GACAUACCGAGCUAAA-3' | 56 |
| 6CTGF AS: 5'-UUUAGCUCGGUAUGUCUUCAU-3' | 57 |
| 7CTGF S: 5'-UCAAGUUGUUCCUUAA-3' | 58 |
| 7CTGF AS: 5'-UUAAGGAACAACUUGACUCAG-3' | 59 |
| 8CTGF S: 5'-AAGACAUACCGAGCUA-3' | 60 |
| 8CTGF AS: 5'-UAGCUCGGUAUGUCUUCAUGC-3' | 61 |
| 9CTGF S: 5'-ACCAGCAGAAAGGUUA-3' | 62 |
| 9CTGF AS: 5'-UAACCUUUCUGCUGGUACCCU-3' | 63 |
| 10CTGF S: 5'-UAAUUGAGAAGGAAAA-3' | 64 |
| 10CTGF AS: 5'-UUUUCCUUCUCAAUUACACUU-3' | 65 |
| 11CTGF S: 5'-ACCGCAAGAUCGGCGU-3' | 66 |
| 11CTGF AS: 5'-ACGCCGAUCUUGCGGUUGGCC-3' | 67 |
| 12CTGF S: 5'-CCAACCAUGACCGCCG-3' | 68 |
| 12CTGF AS: 5'-CGGCGGUCAUGGUUGGCACUG-3' | 69 |
| 13CTGF S: 5'-UGGAGUUCAAGUGCCC-3' | 70 |
| 13CTGF AS: 5'-GGGCACUUGAACUCCACCGGC-3' | 71 |
| 14CTGF S: 5'-ACCCGCACAAGGGCCU-3' | 72 |
| 14CTGF AS: 5'-AGGCCCUUGUGCGGGUCGCAG-3' | 73 |
| 15CTGF S: 5'-UGCCCCUUCCCGAGGA-3' | 74 |
| 15CTGF AS: 5'-UCCUCGGGAAGGGGCAGUCAG-3' | 75 |
| 16CTGF S: 5'-ACAGCUAGGAUGUGCA-3' | 76 |
| 16CTGF AS: 5'-UGCACAUCCUAGCUGUCACUG-3' | 77 |
| 17CTGF S: 5'-CCAACUAUGAUUAGAG-3' | 78 |
| 17CTGF AS: 5'-CUCUAAUCAUAGUUGGGUCUG-3' | 79 |
| 18CTGF S: 5'-UGAAGACAUACCGAGC-3' | 80 |
| 18CTGF AS: 5'-GCUCGGUAUGUCUUCAUGCUG-3' | 81 |
| 19CTGF S: 5'-AGGCUGAUUUCUAGGU-3' | 82 |
| 19CTGF AS: 5'-ACCUAGAAAUCAGCCUGCCAA-3' | 83 |
| 20CTGF S: 5'-CUCCCAAAAUCUCCAA-3' | 84 |
| 20CTGF AS: 5'-UUGGAGAUUUUGGGAGUACGG-3' | 85 |
| 21CTGF S: 5'-ACUGGAAGACACGUUU-3' | 86 |
| 21CTGF AS: 5'-AAACGUGUCUUCCAGUCGGUA-3' | 87 |

TABLE 1-continued

Nucleic acid sequences for exemplary CTGF-targeting asiRNA.

| SEQUENCE | SEQ ID NO: |
|---|---|
| 22CTGF S: 5'-GGGUUACCAAUGACAA-3' | 88 |
| 22CTGF AS: 5'-UUGUCAUUGGUAACCCGGGUG-3' | 89 |
| 23CTGF S: 5'-GACCUGGAAGAGAACA-3' | 90 |
| 23CTGF AS: 5'-UGUUCUCUUCCAGGUCAGCUU-3' | 91 |
| 24CTGF S: 5'-GGAAGAGAACAUUAAG-3' | 92 |
| 24CTGF AS: 5'-CUUAAUGUUCUCUUCCAGGTC-3' | 93 |
| 25CTGF S: 5'-CCAAGCCUAUCAAGUU-3' | 94 |
| 25CTGF AS: 5'-AACUUGAUAGGCUUGGAGAUU-3' | 95 |
| 26CTGF S: 5'-CAUACCGAGCUAAAUU-3' | 96 |
| 26CTGF AS: 5'-AAUUUAGCUCGGUAUGUCUUC-3' | 97 |
| 27CTGF S: 5'-AAAUUCUGUGGAGUAU-3' | 98 |
| 27CTGF AS: 5'-AUACUCCACAGAAUUUAGCUC-3' | 99 |
| 28CTGF S: 5'-CUGGAAGAGAACAUUA-3' | 100 |
| 28CTGF AS: 5'-UAAUGUUCUCUUCCAGGUCAG-3' | 101 |
| 29CTGF S: 5'-UGGAAGAGAACAUUAA-3' | 102 |
| 29CTGF AS: 5'-UUAAUGUUCUCUUCCAGGUCA-3' | 103 |
| 30CTGF S: 5'-UGGAACUUGAACUGAU-3' | 104 |
| 30CTGF AS: 5'-AUCAGUUCAAGUUCCAGUCUA-3' | 105 |
| 31CTGF S: 5'-UUCUCCAGCCAUCAAG-3' | 106 |
| 31CTGF AS: 5'-CUUGAUGGCUGGAGAAUGCAC-3' | 107 |
| 32CTGF S: 5'-CACCAUAGGUAGAAUG-3' | 108 |
| 32CTGF AS: 5'-CAUUCUACCUAUGGUGUUCAG-3' | 109 |
| 33CTGF S: 5'-CGUUCAAAGCAUGAAA-3' | 110 |
| 33CTGF AS: 5'-UUUCAUGCUUUGAACGAUCAG-3' | 111 |
| 34CTGF S: 5'-GUUUUUCGGACAGUUU-3' | 112 |
| 34CTGF AS: 5'-AAACUGUCCGAAAAACAGUCA-3' | 113 |
| 35CTGF S: 5'-AAGAUUCCCACCCAAU-3' | 114 |
| 35CTGF AS: 5'-AUUGGGUGGGAAUCUUUUCCC-3' | 115 |
| 36CTGF S: 5'-GGCAUGAAGCCAGAGA-3' | 116 |
| 36CTGF AS: 5'-UCUCUGGCUUCAUGCCAUGUC-3' | 117 |
| 37CTGF S: 5'-CUCAUUUUUCCGUAAA-3' | 118 |
| 37CTGF AS: 5'-UUUACGGAAAAAUGAGAUGUG-3' | 119 |
| 38CTGF S: 5'-GUCCCGGAGACAAUGA-3' | 120 |
| 38CTGF AS: 5'-UCAUUGUCUCCGGGACAGUUG-3' | 121 |
| 39CTGF S: 5'-AUCGUUCAAAGCAUGA-3' | 122 |
| 39CTGF AS: 5'-UCAUGCUUUGAACGAUCAGAC-3' | 123 |
| 40CTGF S: 5'-UCUAUAUAGCUGAUCA-3' | 124 |
| 40CTGF AS: 5'-UGAUCAGCUAUAUAGAGUCAC-3' | 125 |
| 41CTGF S: 5'-CCGUCCGCGUCGCCUU-3' | 126 |
| 41CTGF AS: 5'-AAGGCGACGCGGACGGGGCCC-3' | 127 |
| 42CTGF S: 5'-CAGCUGGGCGAGCUGU-3' | 128 |
| 42CTGF AS: 5'-ACAGCUCGCCCAGCUGCUUGG-3' | 129 |
| 43CTGF S: 5'-GUGCACCGCCAAAGAU-3' | 130 |
| 43CTGF AS: 5'-AUCUUUGGCGGTGCACACGCC-3' | 131 |
| 44CTGF S: 5'-GAGCAGCUGCAAGUAC-3' | 132 |
| 44CTGF AS: 5'-GUACUUGCAGCUGCUCUGGAA-3' | 133 |
| 45CTGF S: 5'-UGAUUAGAGCCAACUG-3' | 134 |
| 45CTGF AS: 5'-CAGUUGGCUCUAAUCAUAGUU-3' | 135 |
| 46CTGF S: 5'-AGACAUACCGAGCUAA-3' | 136 |
| 46CTGF AS: 5'-UUAGCUCGGUAUGUCUUCAUG-3' | 137 |
| 47CTGF S:5'-ACUCAUUAGACUGGAA-3' | 138 |
| 47CTGF AS: 5'-UUCCAGUCUAAUGAGUUAAUG-3' | 139 |
| 48CTGF S: 5'-AGAUAGCAUCUUAUAC-3' | 140 |
| 48CTGF AS: 5'-GUAUAAGAUGCUAUCUGAUGA-3' | 141 |
| 49CTGF S: 5'-AGAGACUGAGUCAAGU-3' | 142 |
| 49CTGF AS: 5'-ACUUGACUCAGUCUCUUGAUG-3' | 143 |
| 50CTGF S: 5'-AAUGACAGUCCGUCAA-3' | 144 |
| 50CTGF AS: 5'-UUGACGGACUGUCAUUCUAUC-3' | 145 |
| 51CTGF S: 5'-GCCGCGUCUGCGCCAA-3' | 146 |
| 51CTGF AS: 5'-UGGCGCAGACGCGGCAGCAGC-3' | 147 |
| 52CTGF S: 5'-UGUGCAGCAUGGACGU-3' | 148 |
| 52CTGF AS: 5'-ACGUCCAUGCUGCACAGGGGC-3' | 149 |
| 53CTGF S: 5'-CUGUGCAGCAUGGACG-3' | 150 |
| 53CTGF AS: 5'-CGUCCAUGCUGCACAGGGGCA-3' | 151 |
| 54CTGF S: 5'-CCCUGACUGCCCCUUC-3' | 152 |
| 54CTGF AS: 5'-GAAGGGGCAGUCAGGGCUGGG-3' | 153 |
| 55CTGF S: 5'-GCCCUGACUGCCCCUU-3' | 154 |
| 55CTGF AS: 5'-AAGGGGCAGUCAGGGCUGGGC-3' | 155 |
| 56CTGF S: 5'-GUGACGAGCCCAAGGA-3' | 156 |
| 56CTGF AS: 5'-UCCUUGGGCUCGUCACACACC-3' | 157 |
| 57CTGF S: 5'-UGUGUGACGAGCCCAA-3' | 158 |
| 57CTGF AS: 5'-UUGGGCUCGUCACACACCCAC-3' | 159 |
| 58CTGF S: 5'-AGUGGGUGUGUGACGA-3' | 160 |
| 58CTGF AS: 5'-UCGUCACACACCCACUCCUCG-3' | 161 |
| 59CTGF S: 5'-AGGAGUGGGUGUGUGA-3' | 162 |

TABLE 1-continued

Nucleic acid sequences for exemplary CTGF-targeting asiRNA.

| SEQUENCE | SEQ ID NO: |
|---|---|
| 59CTGF AS: 5'-UCACACACCCACUCCUCGCAG-3' | 163 |
| 60CTGF S: 5'-CGAGGAGUGGGUGUGU-3' | 164 |
| 60CTGF AS: 5'-ACACACCCACUCCUCGCAGCA-3' | 165 |
| 61CTGF S: 5'-UGCGAGGAGUGGGUGU-3' | 166 |
| 61CTGF AS: 5'-ACACCCACUCCUCGCAGCAUU-3' | 167 |
| 62CTGF S: 5'-CAGACCCAACUAUGAU-3' | 168 |
| 62CTGF AS: 5'-AUCAUAGUUGGGUCUGGGCCA-3' | 169 |
| 63CTGF S: 5'-CCAGACCCAACUAUGA-3' | 170 |
| 63CTGF AS: 5'-UCAUAGUUGGGUCUGGGCCAA-3' | 171 |
| 64CTGF S: 5'-CCCAGACCCAACUAUG-3' | 172 |
| 64CTGF AS: 5'-CAUAGUUGGGUCUGGGCCAAA-3' | 173 |
| 65CTGF S: 5'-GAGUGGAGCGCCUGUU-3' | 174 |
| 65CTGF AS: 5'-AACAGGCGCUCCACUCUGUGG-3' | 175 |
| 66CTGF S: 5'-GUCCAGACCACAGAGU-3' | 176 |
| 66CTGF AS: 5'-ACUCUGUGGUCUGGACCAGGC-3' | 177 |
| 67CTGF S: 5'-UGGUCCAGACCACAGA-3' | 178 |
| 67CTGF AS: 5'-UCUGUGGUCUGGACCAGGCAG-3' | 179 |
| 68CTGF S: 5'-CCUGGUCCAGACCACA-3' | 180 |
| 68CTGF AS: 5'-UGUGGUCUGGACCAGGCAGUU-3' | 181 |
| 69CTGF S: 5'-AACUGCCUGGUCCAGA-3' | 182 |
| 69CTGF AS: 5'-UCUGGACCAGGCAGUUGGCUC-3' | 183 |
| 70CTGF S: 5'-GGGAUGGGCAUCUCCA-3' | 184 |
| 70CTGF AS: 5'-UGGAGAUGCCCAUCCCACAGG-3' | 185 |
| 71CTGF S: 5'-UGUGGGAUGGGCAUCU-3' | 186 |
| 71C1GF AS: 5'-AGAUGCCCAUCCCACAGGUCU-3' | 187 |
| 72CTGF S: 5'-CUGUGGGAUGGGCAUC-3' | 188 |
| 72CTGF AS: 5'-GAUGCCCAUCCCACAGGUCUU-3' | 189 |
| 73CTGF S: 5'-AGGGCAAAAAGUGCAU-3' | 190 |
| 73CTGF AS: 5'-AUGCACUUUUGCCCUUCUUA-3' | 191 |
| 74CTGF S: 5'-UAAGAAGGGCAAAAAG-3' | 192 |
| 74CTGF AS: 5'-CUUUUUGCCCUUCUUAAUGUU-3' | 193 |
| 75CTGF S: 5'-CUUUCUGGCUGCACCA-3' | 194 |
| 75CTGF AS: 5'-UGGUGCAGCCAGAAAGCUCAA-3' | 195 |
| 76CTGF S: 5'-GAGCUUUCUGGCUGCA-3' | 196 |
| 76CTGF AS: 5'-UGCAGCCAGAAAGCUCAAACU-3' | 197 |
| 77CTGF S: 5'-CUGCCAUUACAACUGU-3' | 198 |
| 77CTGF AS: 5'-ACAGUUGUAAUGGCAGGCACA-3' | 199 |
| 78CTGF S: 5'-GCCUGCCAUUACAACU-3' | 200 |
| 78CTGF AS: 5'-AGUUGUAAUGGCAGGCACAGG-3' | 201 |
| 79CTGF S: 5'-UGCCUGCCAUUACAAC-3' | 202 |
| 79CTGF AS: 5'-GUUGUAAUGGCAGGCACAGGU-3' | 203 |
| 80CTGF S: 5'-GUGCCUGCCAUUACAA-3' | 204 |
| 80CTGF AS: 5'-UUGUAAUGGCAGGCACAGGUC-3' | 205 |
| 81CTGF S: 5'-UGUGCCUGCCAUUACA-3' | 206 |
| 81CTGF AS: 5'-UGUAAUGGCAGGCACAGGUCU-3' | 207 |
| 82CTGF S: 5'-CCUGUGCCUGCCAUUA-3' | 208 |
| 82CTGF AS: 5'-UAAUGGCAGGCACAGGUCUUG-3' | 209 |
| 83CTGF S: 5'-ACCUGUGCCUGCCAUU-3' | 210 |
| 83CTGF AS: 5'-AAUGGCAGGCACAGGUCUUGA-3' | 211 |
| 84CTGF S: 5'-GACCUGUGCCUGCCAU-3' | 212 |
| 84CTGF AS: 5'-AUGGCAGGCACAGGUCUUGAU-3' | 213 |
| 85CTGF S: 5'-GUUCAUCAAGACCUGU-3' | 214 |
| 85CTGF AS: 5'-ACAGGUCUUGAUGAACAUCAU-3' | 215 |
| 86CTGF S: 5'-AGAUGUACGGAGACAU-3' | 216 |
| 86CTGF AS: 5'-AUGUCUCCGUACAUCUUCCUG-3' | 217 |
| 87CTGF S: 5'-GGAAGAUGUACGGAGA-3' | 218 |
| 87CTGF AS: 5'-UCUCCGUACAUCUUCCUGUAG-3' | 219 |
| 88CTGF S: 5'-CUACAGGAAGAUGUAC-3' | 220 |
| 88CTGF AS: 5'-GUACAUCUUCCUGUAGUACAG-3' | 221 |
| 89CTGF S: 5'-ACAGCUUGUGGCAAGU-3' | 222 |
| 89CTGF AS: 5'-ACUUGCCACAAGCUGUCCAGU-3' | 223 |
| 90CTGF S: 5'-GACAGCUUGUGGCAAG-3' | 224 |
| 90CTGF AS: 5'-CUUGCCACAAGCUGUCCAGUC-3' | 225 |
| 91CTGF S: 5'-GGACAGCUUGUGGCAA-3' | 226 |
| 91CTGF AS: 5'-UUGCCACAAGCUGUCCAGUCU-3' | 227 |
| 92CTGF S: 5'-AACAAGCCAGAUUUUU-3' | 228 |
| 92CTGF AS: 5'-AAAAAUCUGGCUUGUUACAGG-3' | 229 |
| 93CTGF S: 5'-GUAACAAGCCAGAUUU-3' | 230 |
| 93CTGF AS: 5'-AAAUCUGGCUUGUUACAGGCA-3' | 231 |
| 94CTGF S: 5'-CUGUAACAAGCCGAU-3' | 232 |
| 94CTGF AS: 5'-AUCUGGCUUGUUACAGGCAAA-3' | 233 |
| 95CTGF S: 5'-UCUAAGUUAAUUUAAA-3' | 234 |
| 95CTGF AS: 5'-UUUAAAUUAACUUAGAUAACU-3' | 235 |
| 96CTGF S: 5'-CACCUUUCUAGUUGAA-3' | 236 |
| 96CTGF AS: 5'-UUCAACUAGAAAGGUGCAAAC-3' | 237 |

TABLE 1-continued

Nucleic acid sequences for exemplary CTGF-targeting asiRNA.

| SEQUENCE | SEQ ID NO: |
|---|---|
| 97CTGF S: 5'-UUGCACCUUUCUAGUU-3' | 238 |
| 97CTGF AS: 5'-AACUAGAAAGGUGCAAACAUG-3' | 239 |
| 98CTGF S: 5'-CAUGUUUGCACCUUUC-3' | 240 |
| 98CTGF AS: 5'-GAAAGGUGCAAACAUGUAACU-3' | 241 |
| 99CTGF S: 5'-GAGUGUGACCAAAAGU-3' | 242 |
| 99CTGF AS: 5'-ACUUUUGGUCACACUCUCAAC-3' | 243 |
| 100CTGF S: 5'-AGAGUGUGACCAAAAG-3' | 244 |

The asiRNAs listed in Table 1 were incubated at 95° C. for 2 minutes and at 37° C. for 1 hour in 1x siRNA duplex buffer (Bioneer Inc., Korea). Proper strand annealing was confirmed via gel electrophoresis. For the screen, $2.5 \times 10^4$ A549 cells (ATCC), that had been cultured in Dulbecco's modified Eagle's medium (Gibco) containing 10% fetal bovine serum (Gibco) and 100 µg/ml penicillin/streptomycin, were seeded into 24-well plates. The A549 cells were transfected with 0.3 nM of the asiRNAs using Lipofectamine 2000 (Invitrogen) according to the manufacturer's instructions.

Twenty-four hours after transfection, CTGF mRNA levels were measured using real-time RT-PCR. Total RNA was extracted using Isol-RNA lysis reagent (SPRIME), and then 500 ng of the extracted RNA was used for cDNA synthesis using the High-capacity cDNA reverse transcription kit (Applied Biosystems), according to the manufacturer's instructions. The synthesized cDNA was diluted and then quantitative RT-PCR was performed using the StepOne RT-PCR system (Applied Biosystems) according to manufacturer's instructions. The level of CTGF inhibition by each of the 100 asiRNAs is depicted in FIG. 1.

Example 2

Inhibition of CTGF MRNA Expression Using CTGF-targeting AsiRNAs

Eighteen of the asiRNA sequences, asiCTGF 4, 9, 16, 25, 30, 32, 33, 34, 39, 40, 48, 49, 81, 92, 93, 96, 97 and 99, were tested for their ability to inhibit CTGF expression.

The selected asiRNAs were incubated at 95° C. for 2 minutes and at 37° C. for 1 hour in 1x siRNA duplex buffer (Bioneer Inc., Korea). Proper strand annealing was confirmed via gel electrophoresis. For the screen, $2.5 \times 10^4$ A549 cells (ATCC) were seeded into 24-well plates. The A549 cells were transfected with 0.3 or 0.1 nM of asiRNAs using Lipofectamine 2000 (Invitrogen) according to the manufacturer's instructions.

The CTGF mRNA levels in the transfected cells were measured 24 hours after transfection using RT-PCR. Specifically, total RNA was extracted using Isol-RNA lysis reagent (5PRIME), and then 500 ng of the extracted RNA was used for cDNA synthesis using High-Capacity cDNA reverse transcription kit (Applied Biosystems). The synthesized cDNA was diluted and then quantitative RT- PCR was performed using the StepOne RT-PCR system (Applied Biosystems). Amplification of the CTGF gene was detected using a power SYBR green PCR master Mix (Applied Biosystems). GAPDH was amplified as an internal control. The following primer sequences were used:

Human GAPDH-forward:
5'-GAG TCA ACG GAT TTG GTC GT-3' (SEQ ID NO: 245)

Human GAPDH-reverse:
5'-GAC AAG CTT CCC GTT CTC AG-3' (SEQ ID NO: 246)

Human CTGF-forward:
5'-CAA GGG CCT CTT CTG TGA CT-3' (SEQ ID NO: 247)

Human CTGF-reverse:
5'-ACG TGC ACT GGT ACT TGC AG-3' (SEQ ID NO: 248)

Figure 2:
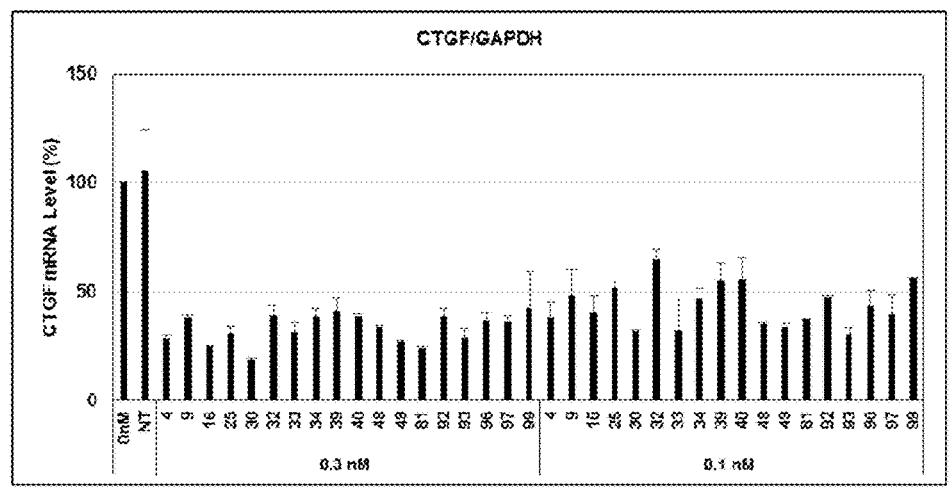
FIG. 2 shows the gene silencing efficiency of 18 exemplary asiRNAs that target CTGF.

The level of CTGF inhibition of 18 exemplary asiRNAs is provided in FIG. 2. As shown in FIG. 2, asiRNAs 4, 9, 16, 30, 33, 34, 48, 49, 81, 92, 93, 96 and 97 inhibited CTGF expression.

Example 3

Inhibition of CTGF MRNA Expression Using CTGF-targeting AsiRNAs

Figure 3:
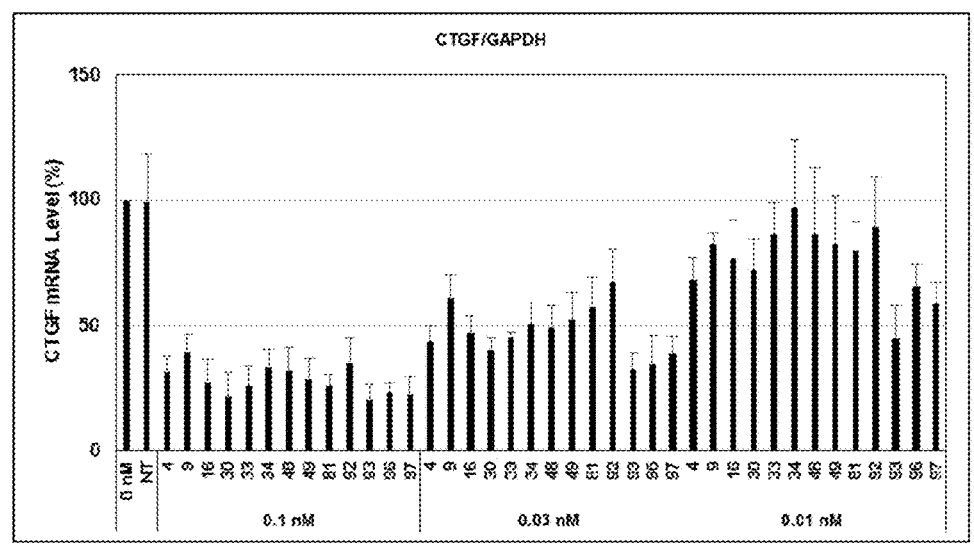
FIG. 3 shows the gene silencing efficiency of 13 exemplary asiRNAs that target CTGF.

Thirteen of the asiRNA sequences, asiCTGF 4, 9, 16, 30, 33, 34, 48, 49, 81, 92, 93, 96 and 97, were tested for their ability to inhibit CTGF expression by transfection.

asiRNAs were incubated at 95° C. for 5 minutes and at 37° C. for 1 hour in 1x siRNA duplex buffer (Bioneer). Proper strand annealing was confirmed via gel electrophoresis. For the screen, A549 cells (ATCC) that had been cultured in Minimum Essential medium (Gibco) containing 10% fetal bovine serum (Gibco) and 100 µg/ml penicillin/ streptomycin in a 100 mm cell culture dish. One day prior to transfection, $2.5 \times 10^4$ A549 cells were seeded into 24-well plates. The A549 cells were transfected with asiRNAs at 0.1, 0.03 and 0.001 nM asiRNA concentrations. Total RNA was extracted using RNAiso Plus (TaKaRa), and then 500 ng of the extracted RNA was used for cDNA synthesis using the High-Capacity cDNA reverse transcription kit (Applied Biosystems), according to the manufacturer's instructions. Amplification of the CTGF gene was detected using a power SYBR Premix Ex Taq (TaKaRa). GAPDH was used as control. The level of CTGF inhibition of 13 asiRNAs is depicted in FIG. 3.

Example 4

Serum Nuclease Stability Using CTGF-targeting AsiRNAs

Figure 4:
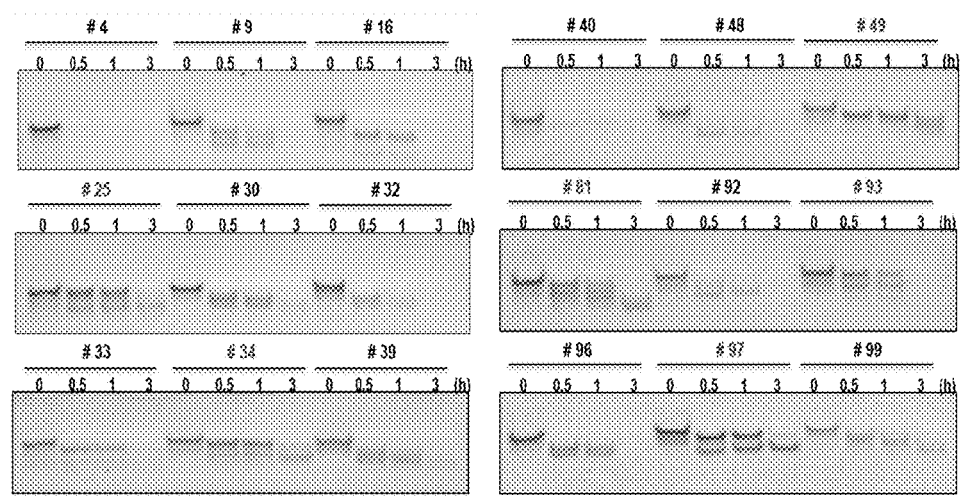
FIG. 4 shows the serum nuclease stability of 18 exemplary asiRNAs that target CTGF.

Selected asiRNAs (0.1 nmole) from Example 1 were incubated in 50 µl of 10% fetal bovine serum solution. Seven microliters of each sample was taken at the indicated time points and immediately frozen at −70° C. A 3 µL aliquot of each sample was then separated in a 10% (wt/vol) non-denaturing polyacrylamide gel, stained with ethidium bromide, and visualized by UV transillumination. The stability of the asiCTGF against serum nuclease is depicted in FIG. 4.

Example 5

Initial Chemical Modification of AsiRNAs for Screening

Chemical modifications of 2'-O-Methyl RNA were applied to asiRNAs selected in Example 1 and the gene silencing efficacy of the modified asiRNAs was tested in A549 cells with naked asiRNA. Modified asiRNAs (Table 2) were screened for CTGF mRNA inhibition A549 cells and CTGF mRNA levels were measured by real-time PCR.

TABLE 2

18 Modified asiRNA sequences tested for efficacy. m = 2'-O-Methyl RNA.

| SEQ ID NO.: | SEQUENCE |
|---|---|
| 1 | 4CTGF-OME 16S: 5'-mCCmAGmAAmUGmUAmUAmUUmAA-3' |
| 2 | 4CTGF-OME 21AS: 5'-UUAAUAUACAUUCUmGmGmUmGmCmUmG-3' |
| 3 | 9CTGF-OME 16S: 5'-mACmCAmGCmAGmAAmAGmGUmUA-3' |
| 4 | 9CTGF-OME 21AS: 5'-UAACCUUUCUGCUGmGmUmAmCmCmCmU-3' |
| 5 | 16CTGF-OME 16S: 5'-mACmAGmCUmAGmGAmUGmUGmCA-3' |
| 6 | 16CTGF-OME 21AS: 5'-UGCACAUCCUAGCUmGmUmCmAmCmUmG-3' |
| 7 | 25CTGF-OME 16S: 5'-mCCmAAmGCmCUmAUmCAmAGmUU-3' |
| 8 | 25CTGF-OME 21AS: 5'-AACUUGAUAGGCUUmGmGmAmGmAmUmU-3' |
| 9 | 30CTGF-OME 16S: 5'-mUGmGAmACmUUmGAmACmUGmAU-3' |
| 10 | 30CTGF-OME 21AS: 5'-AUCAGUUCAAGUUCmCmAmGmUmCmUmA-3' |
| 11 | 32CTGF-OME 16S: 5'-mCAmCCmAUmAGmGUmAGmAAmUG-3' |
| 12 | 32CTGF-OME 21AS: 5'-CAUUCUACCUAUGGmUmGmUmUmCmAmG-3' |
| 13 | 33CTGF-OME 16S: 5'-mCGmUUmCAmAAmGCmAUmGAmAA-3' |
| 14 | 33CTGF-OME 21AS: 5'-UUUCAUGCUUUGAAmCmGmAmUmCmAmG-3' |
| 15 | 34CTGF-OME 16S: 5'-mGUmUUmUmCGmGAmCAmGUmUU-3' |
| 16 | 34CTGF-OME 21AS: 5'-AAACUGUCCGAAAAmAmCmAmGmUmCmA-3' |
| 17 | 39CTGF-OME 16S: 5'-mAUmCGmUUmCAmAAmGCmAUmGA-3' |
| 18 | 39CTGF-OME 21AS: 5'-UCAUGCUUUGAACGmAmUmCmAmGmAmC-3' |
| 19 | 40CTGF-OME 16S: 5'-mUCmUAmUAmUAmGCmUGmAUmCA-3' |
| 20 | 40CTGF-OME 21AS: 5'-UGAUCAGCUAUAUAmGmAmGmUmCmAmC-3' |
| 21 | 48CTGF-OME 16S: 5'-mAGmAUmAGmCAmUCmUUmAUmAC-3' |
| 22 | 48CTGF-OME 21AS: 5'-GUAUAAGAUGCUAUmCmUmGmAmUmGmA-3' |
| 23 | 49CTGF-OME 16S: 5'-mAGmAGmACmUGmAGmUCmAAmGU-3' |
| 24 | 49CTGF-OME 21AS: 5'-ACUUGACUCAGUCUmCmUmUmGmAmUmG-3' |
| 25 | 81CTGF-OME 16S: 5'-mUGmUGmCCmUGmCCmAUmUAmCA-3' |
| 26 | 81CTGF-OME 21AS: 5'-UGUAAUGGCAGGCAmCmAmGmGmUmCmU-3' |
| 27 | 92CTGF-OME 16S: 5'-mAAmCAmAGmCCmAGmAUmUUmUU-3' |

TABLE 2-continued

18 Modified asiRNA sequences tested for efficacy. m = 2'-O-Methyl RNA.

| SEQ ID NO.: | SEQUENCE | |
|---|---|---|
| 28 | 92CTGF-OME 21AS: | 5'-AAAAAUCUGGCUUGmUmUmAmCmAmGmG-3' |
| 29 | 93CTGF-OME 16S: | 5'-mGUmAAmCAmAGmCCmAGmAUmUU-3' |
| 30 | 93CTGF-OME 21AS: | 5'-AAAUCUGGCUUGUUmAmCmAmGmGmCmA-3' |
| 31 | 96CTGF-OME 16S: | 5'-mCAmCCmUUmUCmUAmGUmUGmAA-3' |
| 32 | 96CTGF-OME 21AS: | 5'-UUCAACUAGAAAGGmUmGmCmAmAmAmC-3' |
| 33 | 97CTGF-OME 16S: | 5'-mUUmGCmACmCUmUUmCUmAGmUU-3' |
| 34 | 97CTGF-OME 21AS: | 5'-AACUAGAAAGGUGCmAmAmAmCmAmUmG-3' |
| 35 | 99CTGF-OME 16S: | 5'-mGAmGUmGUmGAmCCmAAmAAmGU-3' |
| 36 | 99CTGF-OME 21AS: | 5'-ACUUUUGGUCACACmUmCmUmCmAmAmC-3' |

The 2'-O-Methyl RNA modified asiRNAs listed in Table 2 were incubated at 95° C. for 2 minutes and at 37° C. for 1 hour in 1x siRNA duplex buffer (Bioneer Inc., Korea). Proper strand annealing was confirmed via gel electrophoresis. For the screen, 2.5×10⁴ A549 cells (ATCC) that had been cultured in Dulbecco's modified Eagle's medium (Gibco) containing 10% fetal bovine serum (Gibco) and 100 μg/ml penicillin/streptomycin in a 100 mm cell culture dish were seeded into 24-well plates. The A549 cells were transfected with 0.1 nM of the modified and naked asiRNAs using Lipofectamine 2000 (Invitrogen) according to the manufacturer's instructions.

Figure 5:
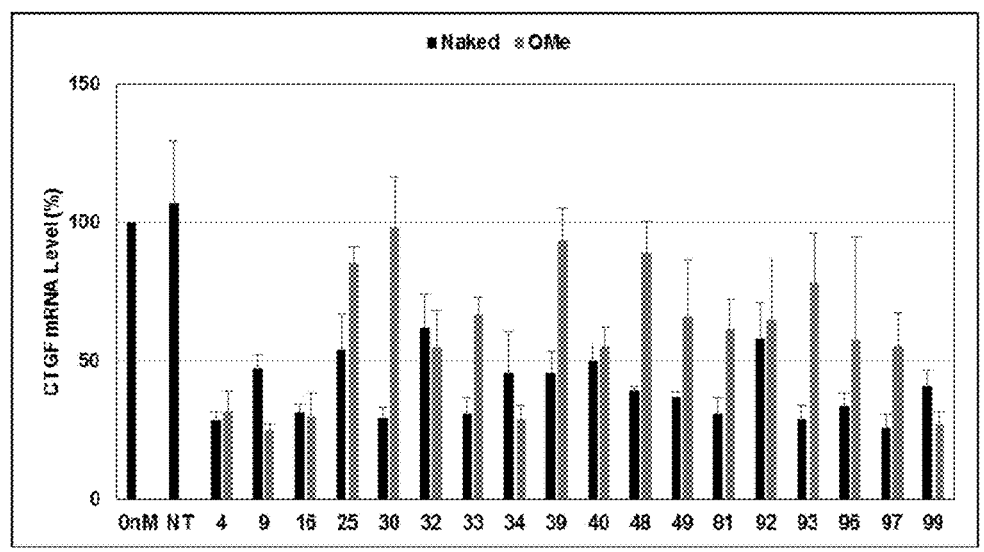
FIG. 5 shows the gene silencing efficiency of 18 exemplary naked and modified asiRNAs that target CTGF.

The CTGF mRNA levels in the transfected cells were measured 24 hours after transfection using RT-PCR. Total RNA was extracted using Isol-RNA lysis reagent (SPRIME), and then 500 ng of the extracted RNA was used for cDNA synthesis using the High-capacity cDNA reverse transcription kit (Applied Biosystems), according to the manufacturer's instructions. The synthesized cDNA was diluted and then quantitative RT-PCR was performed using the StepOne real-time PCR system (Applied Biosystems) according to manufacturer's instructions. The level of CTGF inhibition of naked asiRNA or 2'-O-Methyl RNA modified asiRNAs is shown in FIG. 5.

Example 6

Chemical Modification of AsiRNAs For Self-delivery

Chemical modifications were applied to selected asiRNAs and cellular delivery of modified asiRNAs was tested in the absence of other delivery reagent. As described below, certain of the modifications improved endocytosis and stability of the asiRNAs. Such cell-penetrating asiRNAs (cp-asiRNAs) are able to be delivered into the cell in the absence of a delivery reagent.

Four potential cp-asiRNAs (Table 3) were screened for CTGF mRNA inhibition in A549 cells. A549 cells were incubated at with cp-asiRNAs at 3 μM without a delivery reagent. CTGF mRNA levels were measured by real-time PCR.

TABLE 3

Modified asiRNA sequences tested for self-delivery and CTGF inhibition. m = 2'-O-Methyl RNA. * = phosphorothioate bond. Chol = cholesterol.

| SEQ ID | Sequence | |
|---|---|---|
| 37 | cpCTGF81-16S: | 5'-mUGmUGmCCmUGmCCmAUmUA*mC*A*chol-3' |
| 38 | cpCTGF81-21 AS: | 5'-UGUAAUGGCAGGCAmCmAmG*mG*mU*mC*mU-3' |
| 39 | cpCTGF93-16S: | 5'-mGUmAAmCAmAGmCCmAGmAU*mU*U*chol-3' |
| 40 | cpCTGF93-21AS: | 5'-AAAUCUGGCUUGUUmAmCmA*mG*mG*mC*mA-3' |
| 41 | cpCTGF97-16S: | 5'-mUUmGCmACmCUmUUmCUmAG*mU*U*chol-3' |
| 42 | cpCTGF97-21AS: | 5'-AACUAGAAAGGUGCmAmAmA*mC*mA*mU*mG-3' |
| 43 | cpCTGF99-16S: | 5'-mGAmGUmGUmGAmCCmAAmAA*mG*U*chol-3' |
| 44 | cpCTGF99-21AS: | 5'-ACUUUUGGUCACACmUmCmU*mC*mA*mA*mC-3' |

A549 cells were cultured in Dulbecco's modified Eagle's medium (Gibco) containing 10% fetal bovine serum (Gibco) and 100 μg/ml penicillin/streptomycin in a 100 mm cell culture dish. The potential cp-asiRNAs listed in Table 3 were incubated at 95° C. for 5 minutes and at 37° C. for 1 hour in OPTI-MEM buffer (Gibco). Proper strand annealing was confirmed via gel electrophoresis. One day prior to cp-asiRNA treatment, 2.5×10$^4$ cells were seeded into 24 well plates. Before treatment, the A549 cells were washed with Dulbecco's modified Eagle's medium (Gibco) then cultured in the presence of the potential cp-asiRNAs in OPTI-MEM buffer for 24 hours, at each point the asiRNA-containing OPTI-MEM media was replaced with a serum-containing media. The level of CTGF mRNA expression was determined using real-time PCR 48 hours after asiRNA treatment.

Example 7

Inhibition of CTGF MRNA Expression Using CTGF-targeting Cp-asiRNAs

Inhibition of CTGF mRNA by cp-asiRNAs was tested. Each potential cp-asiRNA was incubated with A549 cells at 3 μM without a delivery reagent and CTGF mRNA levels were measured using real-time PCR.

CTGF cells (ATCC) were cultured in Dulbecco's modified Eagle's medium (Gibco) containing 10% fetal bovine serum (Gibco) and 100 μ/ml penicillin/streptomycin in a 100 mm cell culture dish. The cp-asiRNAs were incubated at 95° C. for 5 minutes and at 37° C. for 1 hour in OPTI-MEM buffer (Gibco). Proper strand annealing was confirmed via gel electrophoresis. One day prior to transfection, 2.5×10$^4$A549 cells were seeded into 24-well plates. Immediately before treatment, the A549 cells were washed with Dulbecco's modified Eagle's medium (Gibco) then cultured in the presence of the potential cp-asiRNAs in OPTI-MEM buffer for 24 hours, at which point the asiRNA-containing OPTI-MEM media was replaced with a serum-containing media. The levels of CTGF mRNA expression were determined 48 hours after asiRNA treatment by real-time PCR. Total RNA was extracted using RNAiso Plus (TaKaRa), and then 500 ng of the extracted RNA was used for cDNA synthesis using the High-Capacity cDNA reverse transcription kit (Applied Biosystems), according to the manufacturer's instructions. Amplification of the CTGF gene was detected using a power SYBR Premix Ex Taq (TaKaRa). GAPDH was amplified as an internal control.

Figure 6:
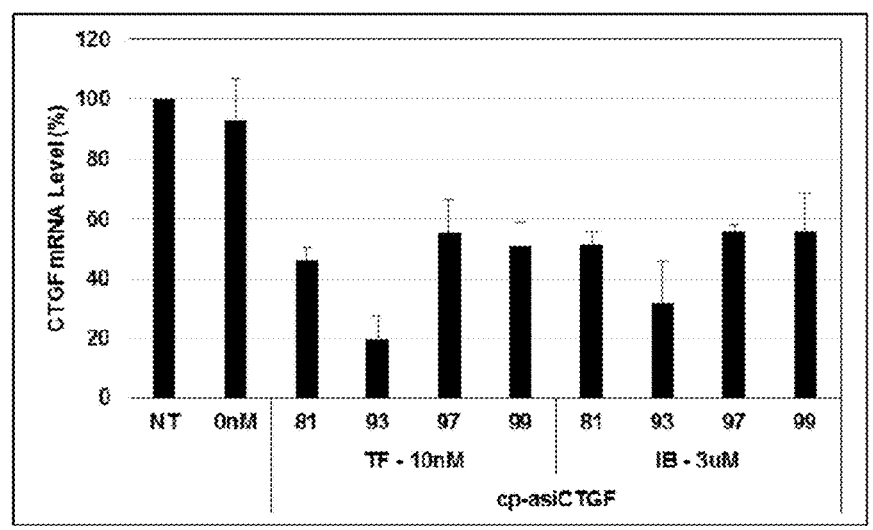
FIG. 6 shows the gene silencing efficiency of exemplary CTGF-targeting cell penetrating asiRNAs (cp-asiRNAs, or cp-asiCTGFs).

The level of CTGF mRNA inhibition by each of the 4 potential cp-asiRNAs is depicted in FIG. 6. In all cp-asiCTGFs incubated cell lines at 45% CTGF protein inhibition was observed, with cp-asiCTGF93 having the highest efficacy in inhibition at the mRNA level.

Example 8

Inhibition of CTGF Protein Expression Using CTGF Targeting Cp-asiRNAs

In order to test inhibition of CTGF protein by cp-asiR-NAs, each potential cp-asiRNA was incubated with A549 cells at 3 μM without a delivery reagent. A549 cells (ATCC) that had been cultured in Dulbecco's modified Eagle's medium (Gibco) containing 10% fetal bovine serum (Gibco) and 100 μg/ml penicillin/streptomycin in a 100 mm cell culture dish.

The cp-asiRNAs were incubated at 95° C. for 5 minutes and at 37° C. for 1 hour in OPTI-MEM buffer (Gibco). Proper strand annealing was confirmed via gel electrophoresis. One day prior to transfection, 9×10$^4$A549 cells were seeded into 6-well plates.

Immediately before treatment, the A549 cells were washed with Dulbecco's modified Eagle's medium (Gibco) then cultured in the presence of cp-asiRNAs in OPTI-MEM buffer for 24 hours, at which point the asiRNA-containing OPTI-MEM media was replaced with a serum-containing media.

Figure 7:
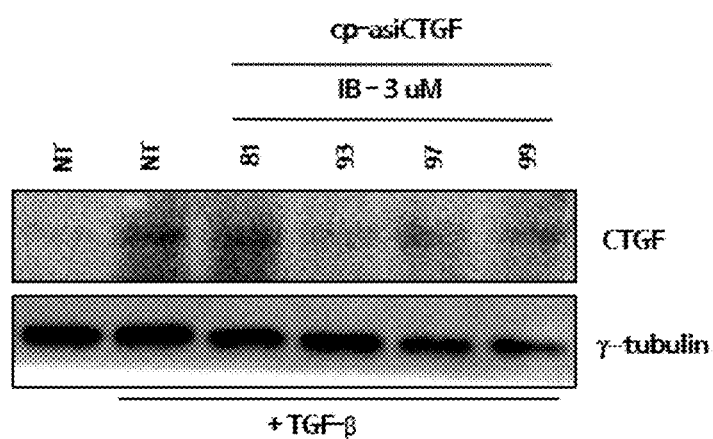
FIG. 7 shows the inhibition of CTGF protein expression by exemplary cp-asiRNAs.

The levels of CTGF protein expression were determined via western blot 48 hours after of asiRNA treatment. Briefly, the treated CTGFH cells were lysed with SDS lysis buffer (1% SDS, 100 mM Tris (pH 8.8)). 20 μg of the total protein extracts were loaded onto a 10% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 3% BSA (Bioworld) and then incubated overnight at 4° C. in 3% BSA containing anti-CTGF antibody (Santa Cruz) and anti-γ-Tubulin antibody (Bethyl). The membrane was then washed with 1× TBST for 10 minutes three times and was incubated for 1 hour at the room temperature in 1× TBST with HRP-conjugated secondary antibody. The membrane was washed with 1x TBST for 10 minutes and treated with 1x ECL for 1 minute. The CTGF and γ-Tubulin bands were then imaged using a Chemidoc instrument (Bio-rad). The results of the western blot assay are depicted in FIG. 7.

Example 9

Inhibition of CTGF by Cp-asiCTGF in an Animal Model

The efficacy of cp-asiCTGF 93 for the inhibition of CTGF expression was evaluated in an animal model. SD rats (males, 6-8 weeks old) were purchased from Orient Bio (Korea). Concentration of 0.4, 0.7, or 1 mg of cp-asiRNA was injected into rat skin and, after 72 hours, skin biopsy samples were collected from the injection sites and subjected to qRT-PCR analysis in order to assess the protein level of CTGF.

Seventy-two hours after cp-asiRNA treatment, total proteins were extracted using Mammalian Protein Extraction Buffer (GE Healthcare) and protease inhibitor cocktail (Roche). The protein concentration was measured using a Bradford assay kit. Equal amounts of protein were resolved via SDS-PAGE gel electrophoresis. After electrophoresis, the proteins were transferred to PVDF membrane (Bio-rad) already activated by methanol (Merck) for 1 hour. The membrane was blocked for 1 hour at room temperature with 5% skim milk and then incubated overnight at 4° C. in 5% skim milk containing specific antibodies (Anti-CTGF antibody: Novus and Santa Cruz, anti-β-Actin antibody: Santa Cruz, anti-GAPDH antibody: Santa Cruz). The membrane was washed with Tris-buffered saline containing 1% Tween-20 and incubated for 1 hour at room temperature in 5% skim milk with HRP-conjugated secondary antibody (Santa Cruz). After incubation, the membrane was treated with ECL substrate (Thermo scientific). The target protein bands were then imaged using a Chemidoc instrument (Bio-rad).

Figure 8:
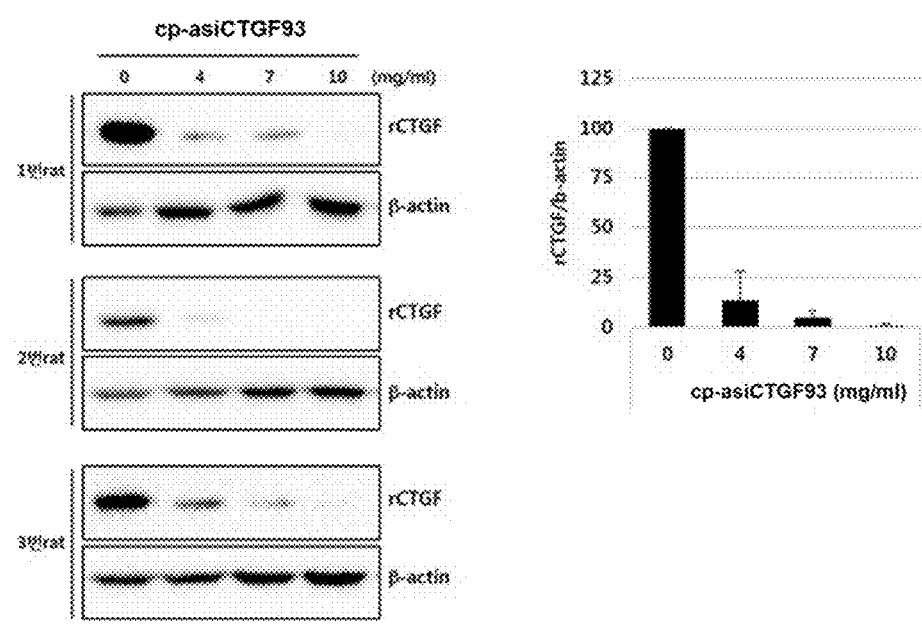
FIG. 8 shows the inhibition of CTGF protein expression by exemplary cp-asiRNAs in Rat skin.

As shown in FIG. 8, a 0.4 mg/injection of cp-asiCTGFs 93 resulted in a greater than 80% reduction in CTGF protein level.

Example 10

Effect of Cp-asiCTGF 93 on the Expression of CTGF in a Bleomycin-induced Lung Fibrosis Animal Model The efficacy of cp-asiCTGF 93 for the inhibition of CTGF expression was evaluated in a bleomycin-induced (BLM) lung fibrosis animal model.

Seven week old male C57BL/6 mice were purchased from Orient Bio (Seongnam, Korea). The mice were anesthetized by intraperitoneal administration of Zoletil 50. Bleomycin sulfate (Enzo, Farmingdale, N.Y.) was dissolved in 1X saline and intratracheally administered as a single dose of 2 mg per kg body weight. Control animals were administered saline only.

After seven days, the cp-asiCTGF 93 was incubated at 95° C. for 5 minutes and at 37° C. for 30 minutes in 0.6X saline. Subsequently, cp-asiCTGF 93 was intratracheally administered into the bleomycin-treated mice (BLM treated mice). Thirty mice were randomly assigned into six groups: negative control mice administered 0.6X saline (n=4), BLM mice administered bleomycin (n=5), 6.2 mpk mice administered bleomycin and 6.2 mg/kg of cp-asiCTGF 93 (n=5), 3.1 mpk mice administered bleomycin and 3.1 mg/kg of cp-asiCTGF 93 (n=6), 1.5 mpk mice administered bleomycin and 1.5 mg/kg of cp-asiCTGF 93 (n=5), and 0.75 mpk mice administered bleomycin and 0.75 mg/kg of cp-asiCTGF 93 (n=5).

Fourteen days after bleomycin administration, the mice were sacrificed and the levels of CTGF mRNA were measured using quantitative RT-PCR. The right lung was used for real-time PCR (RT-PCR) to determine mRNA levels.

Total RNA was extracted from the lung tissues using RNAiso Plus (TaKaRa, Japan), and 500 ng of the extracted RNA was used for cDNA synthesis using the High-Capacity cDNA reverse transcription kit (Applied Biosystems), according to the manufacturer's instructions. The primer and probe sequences used are provided in Table 4. Real time RT-PCR was performed with a power SYBR Premix Ex Taq (TaKaRa, Japan) for CTGF or THUNDERBIRD® Probe qPCR Mix (TOYOBO, Japan) for 18S according to manufacturer's instructions. The housekeeping gene 18S was used as an internal control and gene-specific mRNA expression was normalized against 18S expression.

TABLE 4

4-Primer sequences and probe information for real time reverse transcriptase polymerase chain reaction.

| Gene | Primer Sequences 5' to 3' | | (SEQ ID NO:) |
|---|---|---|---|
| CTGF | Forward | TGCAGTGGGAATTGTGACCT | 249 |
| | Reverse | GGA ATCGGACCTTACCCTGA | 250 |
| Probe | 18S TaqMan | Probe (Hs03928985_g1) | |

Figure 9:
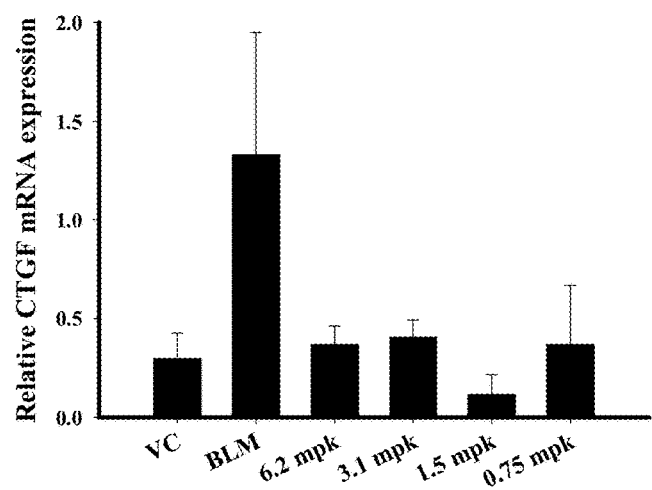
FIG. 9 shows the gene silencing efficiency of cp-asiCTGF 93 that target CTGF in bleomycin treated mice (BLM-treated mice).

As shown in FIG. 9, the expression of BLM-induced upregulation of CTGF expression was significantly inhibited by a single intratracheal administration of cp-asiCTGF 93. A single intratracheal administration of cp-asiCTGF 93 reduced the CTGF mRNA in BLM-treated mice by >60% in comparison with the BLM-treated group.

Example 11

Effect of Cp-asiCTGF 93 on the Expression of Fibrosis Related Genes in a Bleomycin-induced Lung Fibrosis Animal Model The effect of cp-asiCTGF 93 treatment on the expression of fibrosis related genes was evaluated in a bleomycin-induced lung fibrosis animal model.

The cp-asiCTGF 93 was intratracheally administered once 7 days after bleomycin administration (2 mg/kg body weight). The expression level of fibrosis related genes was determined using real-time PCR 14 days after bleomycin administration.

Total RNA was extracted from the lung tissues using RNAiso Plus (TaKaRa, Japan) according to the manufacturer's protocol. The primer sequences used are provided in Table 5. Real time RT-PCR was performed with a power SYBR Premix Ex Taq (TaKaRa, Japan) or THUNDER-BIRD® Probe qPCR Mix (TOYOBO, Japan), and the reactions were conducted on a Applied Biosystems StepOne Real-Time PCR machine (Applied Biosystems, USA). The housekeeping gene 18S was used as an internal control and gene-specific mRNA expression was normalized against 18S expression.

TABLE 5

Primer sequences for real time reverse transcriptase polymerase chain reaction.

| Gene | | Primer Sequences 5' to 3' | (SEQ ID NO:) |
|---|---|---|---|
| Collagen Type-I | Forward | TCATCGTGGCTTCTCTGGTC | 251 |
| | Reverse | GACCGTTGAGTCCGTCTTTG | 252 |
| Collagen Type-III | Forward | ACGTAAGCACTGGTGGACAGA | 253 |
| | Reverse | GAGGGCCATAGCTGAACTGA | 254 |
| Fibronectin | Forward | GTGTAGCACAACTTCCAAT-TACGAA | 255 |
| | Reverse | GGAATTTCCGCCTCGAGTCT | 256 |

Figure 10:
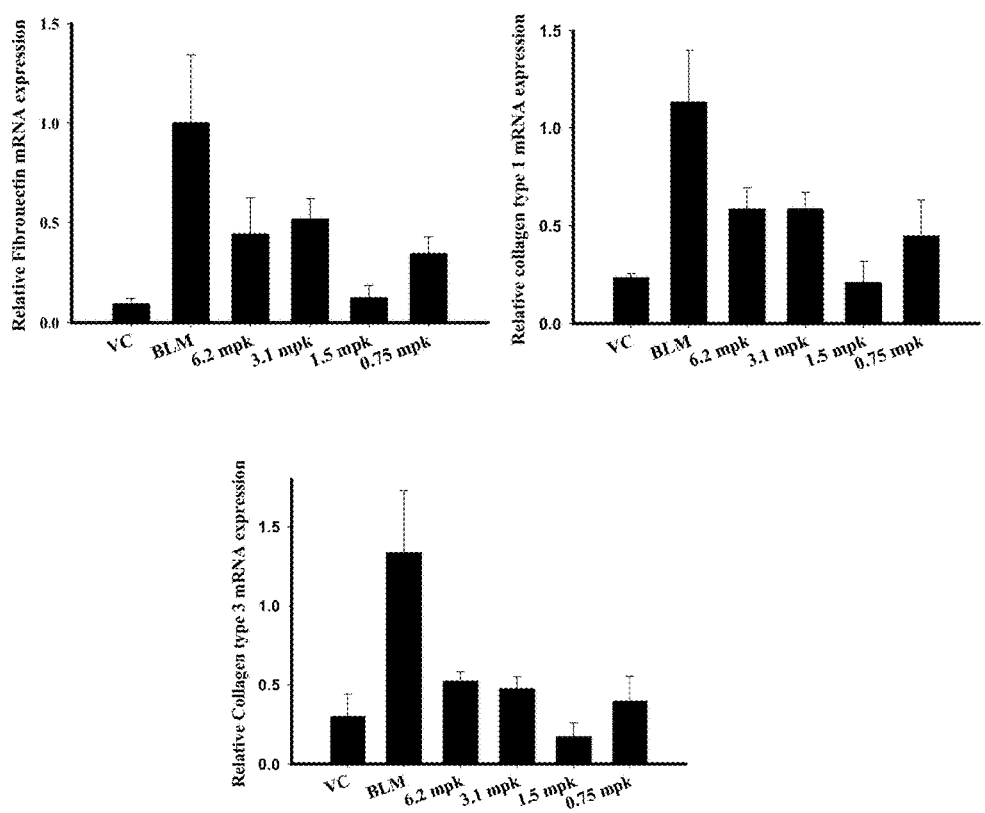
FIG. 10 shows the inhibition of fibrosis related genes expression by cp-asiCTGF 93 in BLM-treated mice.

As shown in FIG. 10, the BLM-induced upregulation of the expression of Fibronectin, collagen type-I and collagen type-III was significantly inhibited by the administration of cp-asiCTGF 93.

Example 12

Effect of Cp-asiCTGF 93 on the Production of Fibronectin Protein in Bleomycin-induced Lung Fibrosis Animal Model The effect of cp-asiCTGF 93 treatment on fibronectin protein level was assessed in a bleomycin-induced lung fibrosis animal model.

The cp-asiCTGF 93 (6.2~0.75 mg/kg body weight) was intratracheally administered once 7 days after bleomycin administration (2 mg/kg body weight). Mice were sacrificed and evaluated 14 days after bleomycin administration. The expression of fibronectin in fibrotic lung tissue was determined using western blot analysis.

To detect fibronectin and gamma tubulin, the samples were homogenized in 500 μL of mammalian protein extraction buffer (GE healthcare). The protein concentration was determined using a Bradford assay. Twenty μg of the total protein extracts were electrophoresed by SDS-PAGE on 10% gels, transferred to polyvinylidene difluoride (PVDF) filters (Bio-Rad, USA) already activated by methanol (Merck) for 1 hour at 300 mA. The membrane was blocked for 1 hour at the room temperature with 5% skim milk and then incubated for overnight at 4° C. with 5% BSA (Bioword) containing mouse anti-fibronectin (Abcam Inc, Cambridge, Mass.) or anti-Gamma tubulin (Santa Cruz Biotechnology, Santa Cruz, Calif.) antibodies. The primary antibodies were detected with horseradish peroxidase-conjugated second antibodies against mouse or rabbit IgG and Chemidoc instrument (Bio-Rad).

Figure 11:
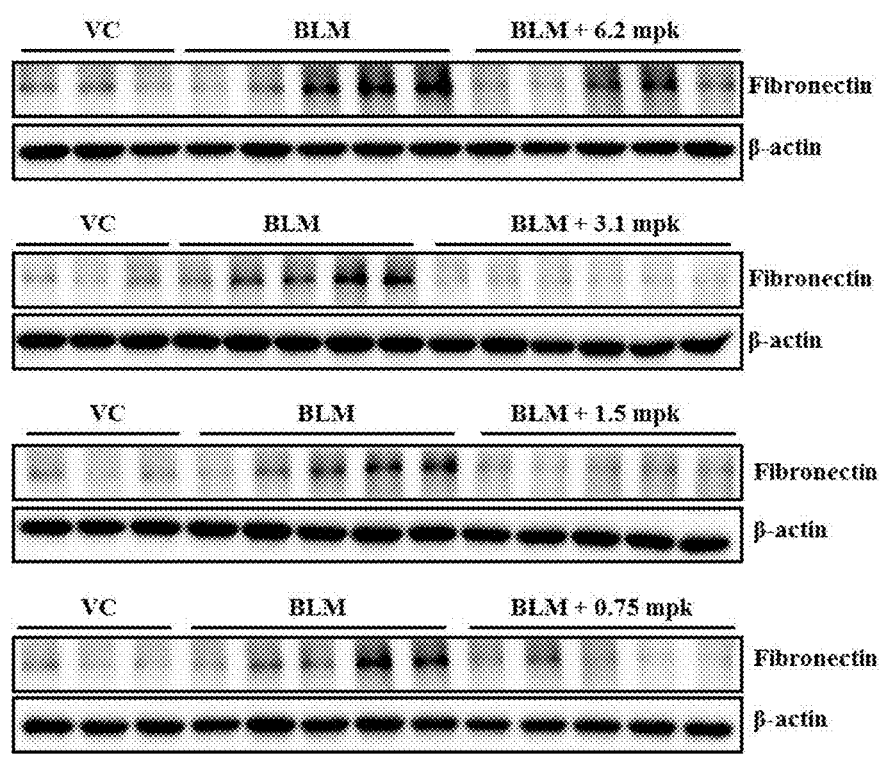
FIG. 11 shows the inhibition of production of fibrosis related proteins by cp-asiCTGF 93 in BLM-treated mice.

As shown in FIG. 11, the BLM-induced upregulation of the expression of fibronectin protein was significantly inhibited by the administration of cp-asiCTGF 93.

Example 13

Effect of Target Gene Knockdown by Cp-asiRNAs with Different Antisense Strands.

Connective tissue growth factor (CTGF) targeting cp-asiRNAs with different antisense strand lengths were tested for efficiency. Sequence and chemical modification of CTGF targeting cp-asiRNAs can be found in Table 6 below.

TABLE 6

| CTGF Exemplary cp-asiRNAs | | | SEQ ID NO: |
|---|---|---|---|
| 21-mer AS | | ***  | |
| | SS | 5'-CUUACCGACUGGAAGAchol-3' | 257 |
| | AS | 3'-GCGCCGAAUGGCUGACCUUCU-5' | 258 |
| | | ****  | |
| 23-mer AS | | *** | |
| | SS | 5'-CUUACCGACUGGAAGAchol-3' | 257 |
| | AS | 3'-GAGCGCCGAAUGGCUGACCUUCU-5' | 259 |
| | | **** | |
| 25-mer AS | | *** | |
| | SS | 5'-CUUACCGACUGGAAGAchol-3' | 257 |
| | AS | 3'-GGGAGCGCCGAAUGGCUGACCUUCU-5' | 260 |
| | | **** | |
| 27-mer AS | | *** | |
| | SS | 5'-CUUACCGACUGGAAGAchol-3' | 257 |
| | AS | 3'-ACGGGAGCGCCGAAUGGCUGACCUUCU-5' | 261 |
| | | **** | |
| 29-mer AS | | *** | |
| | SS | 5'-CUUACCGACUGGAAGAchol-3' | 257 |
| | AS | 3'-GGACGGGAGCGCCGAAUGGCUGACCUUCU-5' | 262 |
| | | **** | |
| 31-mer AS | | *** | |
| | SS | 5'-CUUACCGACUGGAAGAchol-3' | 257 |
| | AS | 3'-CCGGACGGGAGCGCCGAAUGGCUGACCUUCU-5' | 263 |
| | | **** | |

SS: Sense strand, AS: Antisense strand, Underlinedletter: 2'-O-methyl modified RNA
*: Phosphorothioate bond, chol: Cholesterol triethylenleglycol (TEG)

Figure 12A:
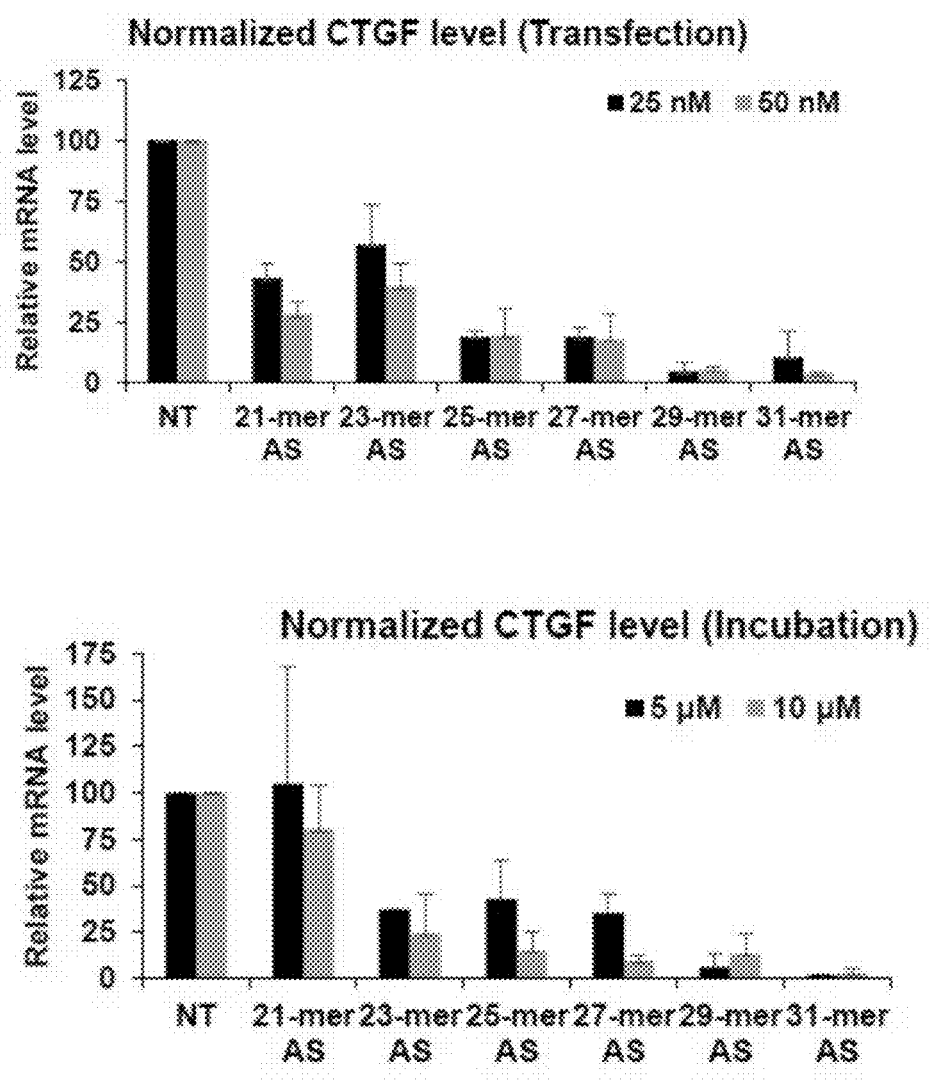
FIG. 12A shows gene silencing activity of CTGF targeting cp-asiRNAs in A549 cells.

Target gene silencing activity of CTGF targeting cp-asiRNAs with varying antisense strand length can be found in FIG. 12A. A549 cells were transfected and incubated with CTGF targeting cp-asiRNAs. Total RNA was extracted from cell lysates and analyzed via quantitative real time polymerase chain reaction (qRT-PCR). Potent target gene silencing of cp-asiRNAs was observed. NT represents no treatment control.

Figure 12B:
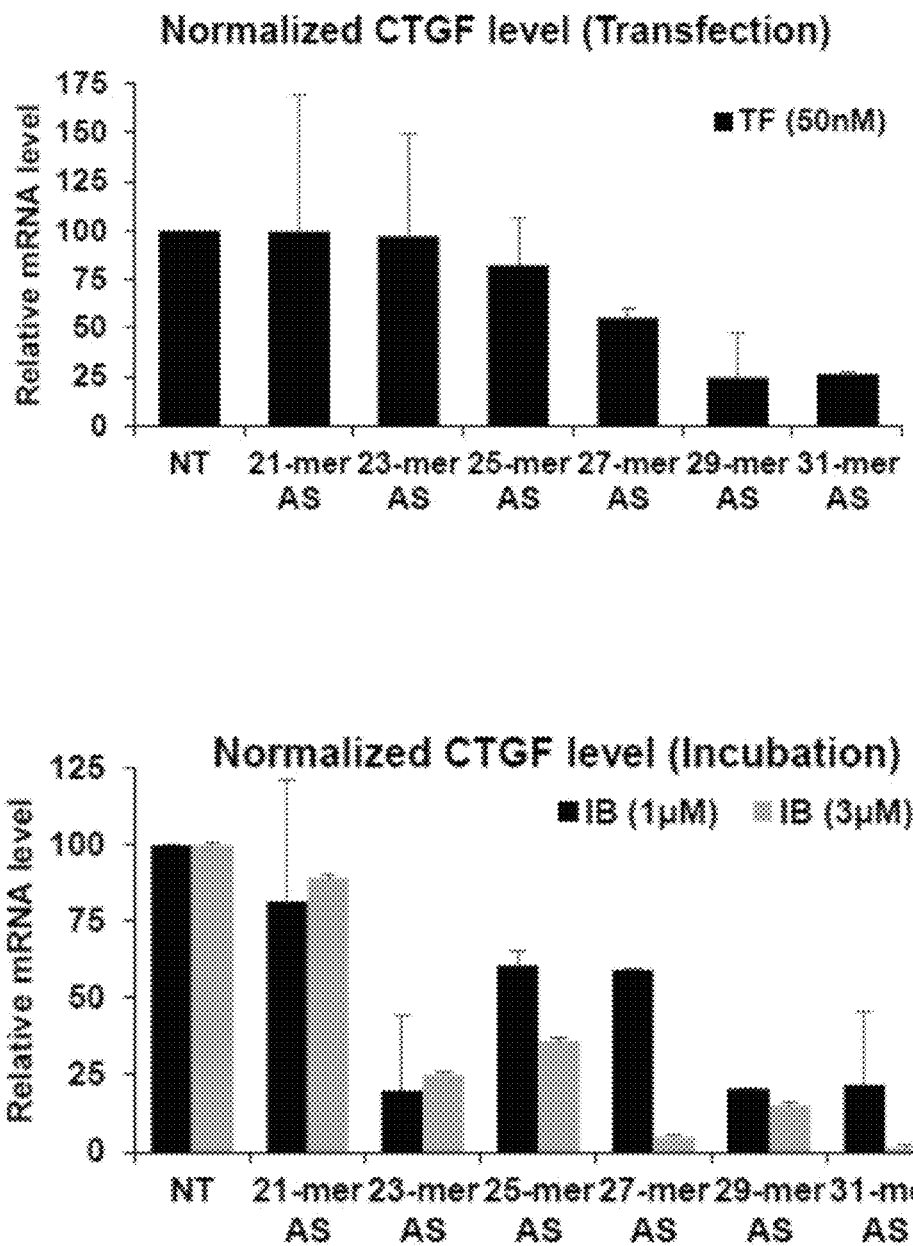
FIG. 12B shows additional gene silencing activity of CTGF targeting cp-asiRNAs in HaCaT cells.
Figure 12C:
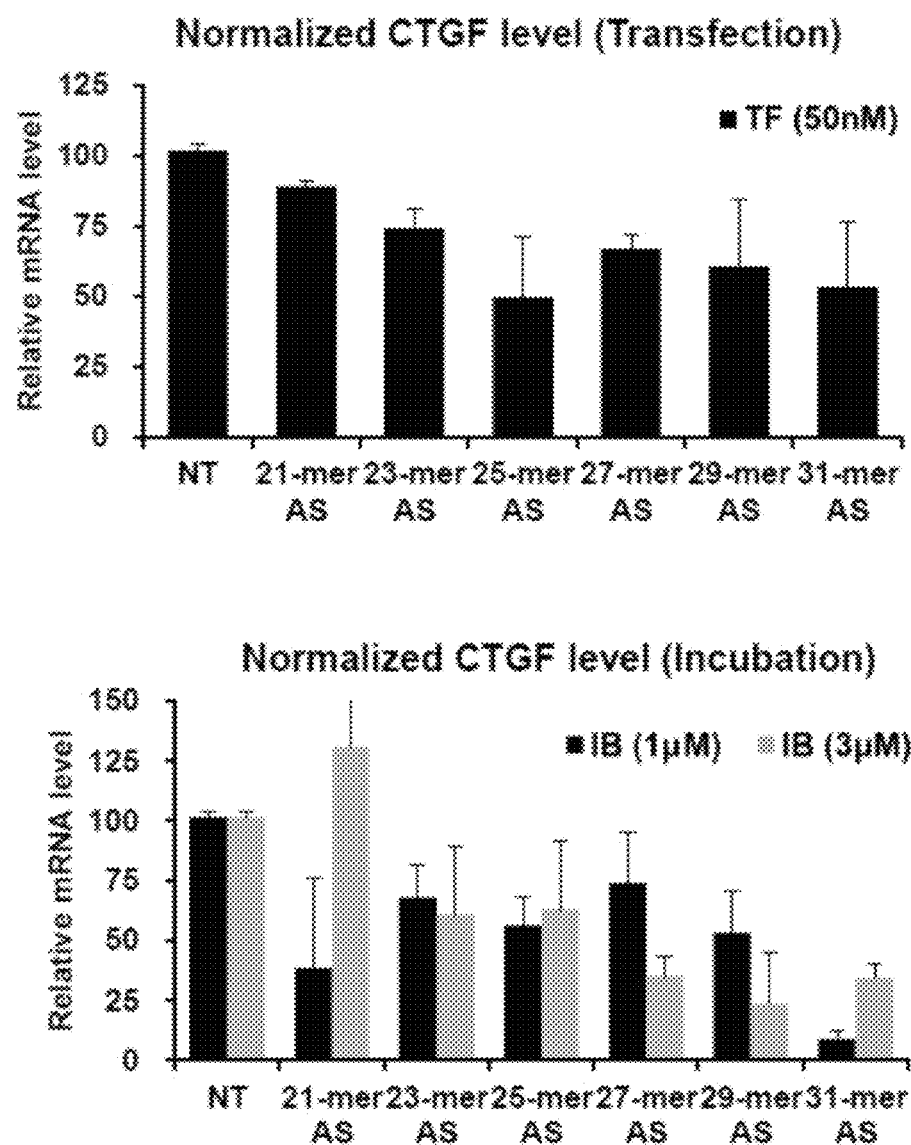
FIG. 12C shows gene silencing activity of CTGF targeting cp-asiRNAs in Hs68 cells.

Target gene silencing activity of CTGF targeting cp-asiRNAs with different antisense strand length in HaCaT cells can be found in FIG. 12B. HaCaT cells were transfected with CTGF targeting cp-asiRNAs. The HaCaT cells were incubated with CTGF targeting cp-asiRNAs. Total RNA was extracted from cell lysates and analyzed via quantitative real time polymerase chain reaction (qRT-PCR). Potent target gene silencing of cp-asiRNAs was observed. NT represents no treatment control. Target gene silencing activity of CTGF targeting cp-asiRNAs in Hs68 cells can be found in FIG. 12C. Hs68 cells were transfected/incubated with CTGF targeting cp-asiRNAs presented above. Total RNA was extracted from cell lysates and processed via quantitative real time polymerase chain reaction (qRT-PCR). Potent target gene silencing of cp-asiRNAs was observed.

Example 14

Effect of in vivo Target Gene Knockdown by Intradermal Injection

Connective tissue growth factor (CTGF) targeting cp-asiRNAs with different antisense strand lengths were tested for efficacy. Sequence and chemical modification of CTGF targeting cp-asiRNAs in Table 6.

Figure 13:
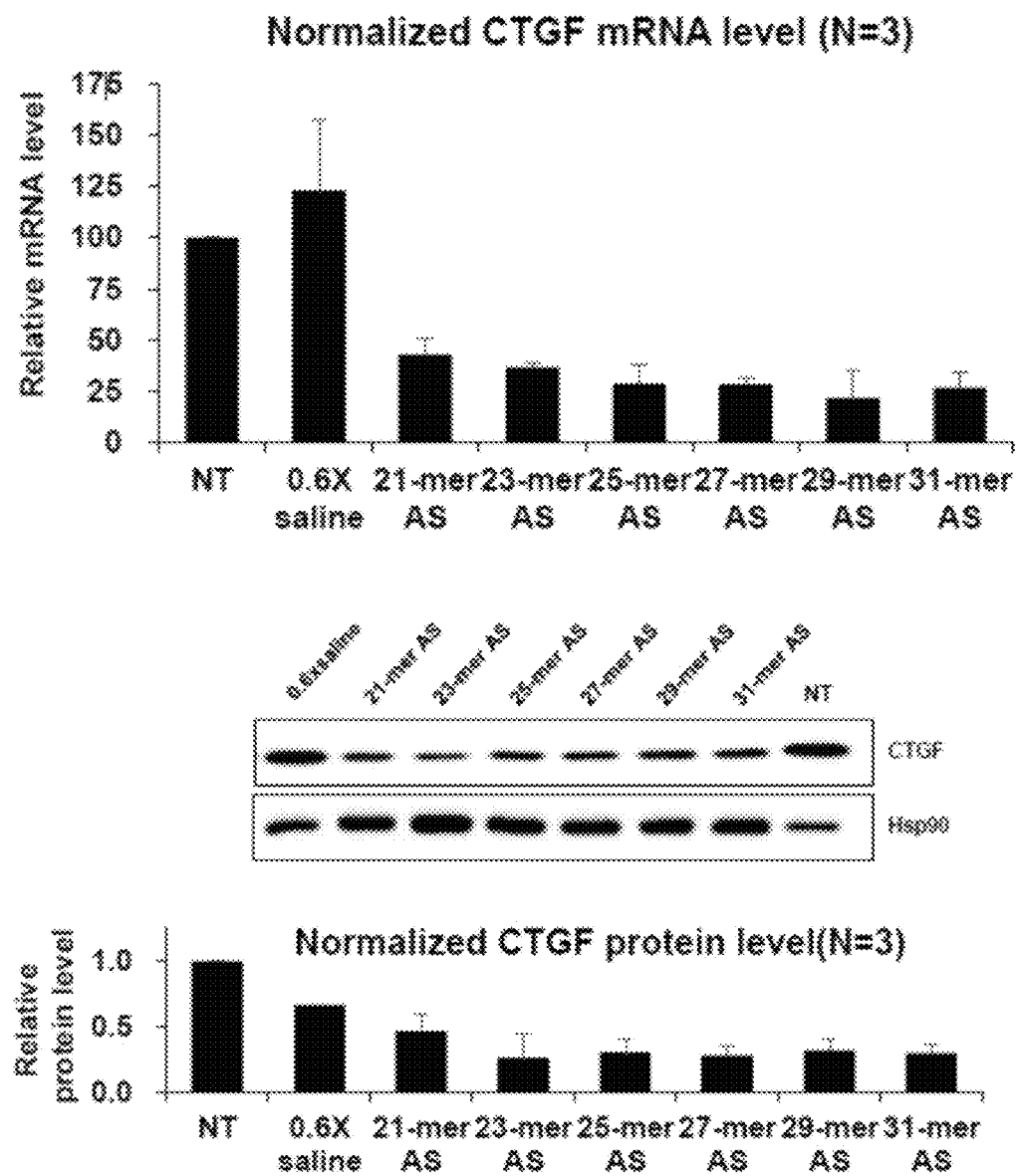
FIG. 13 shows target gene silencing activity of CTGF targeting cp-asiRNAs.

Target gene silencing activity of CTGF targeting cp-asiRNAs with different antisense strand lengths were tested in rat skin (Table 6). 0.5 mg of CTGF targeting cp-asiRNAs in 0.6X saline was injected into rat skin (intradermal injection). FIG. 13 shows target mRNA and protein levels after cp-asiRNAs administration. Potent target gene silencing of cp-asiRNAs was observed. In addition, cp-asiRNAs with longer antisense strands showed the largest target gene knockdown. NT represents no treatment control. 0.6X saline represents reagent only control. These results show target gene knockdown by cp-asiRNA treatment in vivo.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An RNA complex comprising
    an antisense strand that has the nucleotide sequence of SEQ ID NO: 262 that is 29 nt in length and having sequence complementarity to an CTGF mRNA sequence; and
    a sense strand of 15 to 17 nt in length having sequence complementarity to the antisense strand,
    wherein the antisense strand and the sense strand form a complex in which the 5' end of the antisense strand and the 3' end of the sense strand form a blunt end.

2. The RNA complex of claim 1, wherein the sense strand is of 16 nt in length.

3. The RNA complex of claim 2, wherein the sense strand has the nucleotide sequence of SEQ ID NO: 257.

4. The RNA complex of claim 1 or 2, wherein the RNA complex comprises a chemical modification.

5. The RNA complex of claim 4, wherein the chemical modification is a 2'-O-methylated nucleoside, a phosphorothioate bond or a hydrophobic moiety.

6. The RNA complex of claim 5, wherein the RNA complex comprises a hydrophobic moiety.

7. The RNA complex of claim 6, wherein the hydrophobic moiety is a cholesterol moiety.

8. The RNA complex of claim 4, wherein the RNA complex is capable of penetrating the cellular membrane of a cell in the absence of a delivery vehicle.

9. A method of treating idiopathic pulmonary fibrosis in a subject comprising administering to the subject an RNA complex of claim 1 or 2.

10. The method of claim 9, comprising administering the RNA complex to the respiratory tract of the subject.

11. The method of claim 9, wherein the RNA complex is administered intravenously, parenterally, or by inhalation.

12. A pharmaceutical composition comprising an RNA complex of claim 1 or 4 and a pharmaceutically acceptable carrier.

* * * * *

SEQUENCE LISTING

<160> NUMBER OF SEQ ID NOS: 263

<210> SEQ ID NO 1

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ccagaaugua uauuaa                                                       16

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uuaauauaca uucuggugcu g                                                 21

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
accagcagaa agguua                                                       16

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uaaccuuucu gcugguaccc u                                                 21

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
acagcuagga ugugca                                                       16

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugcacauccu agcugucacu g                                                 21

<210> SEQ ID NO 7
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ccaagccuau caaguu                                                         16

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aacuugauag gcuuggagau u                                                   21

<210> SEQ ID NO 9
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uggaacuuga acugau                                                         16

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aucaguucaa guuccagucu a                                                   21

<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
caccauaggu agaaug                                                         16

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cauucuaccu augguguuca g                                                   21

<210> SEQ ID NO 13
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 13
cguucaaagc augaaa                                                     16

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuucaugcuu ugaacgauca g                                               21

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
guuuuucgga caguuu                                                     16

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
aaacuguccg aaaaacaguc a                                               21

<210> SEQ ID NO 17
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aucguucaaa gcauga                                                     16

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ucaugcuuug aacgaucaga c                                               21

<210> SEQ ID NO 19
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 19
ucuauauagc ugauca                                                     16

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugaucagcua uauagaguca c                                               21

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
agauagcauc uuauac                                                     16

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
guauaagaug cuaucugaug a                                               21

<210> SEQ ID NO 23
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
agagacugag ucaagu                                                     16

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
acuugacuca gucucuugau g                                               21

<210> SEQ ID NO 25
<211> LENGTH: 16
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 25
ugugccugcc auuaca                                                        16

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uguaauggca ggcacagguc u                                                  21

<210> SEQ ID NO 27
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aacaagccag auuuuu                                                        16

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaaaucugg cuuguuacag g                                                  21

<210> SEQ ID NO 29
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
guaacaagcc agauuu                                                        16

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aaaucuggcu uguuacaggc a                                                  21

<210> SEQ ID NO 31
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 31
caccuuucua guugaa                                                      16

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uucaacuaga aaggugcaaa c                                                21

<210> SEQ ID NO 33
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uugcaccuuu cuaguu                                                      16

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
aacuagaaag gugcaaacau g                                                21

<210> SEQ ID NO 35
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
gagugugacc aaaagu                                                      16

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
acuuuugguc acacucucaa c                                                21

<210> SEQ ID NO 37
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 37
ugugccugcc auuaca                                                       16

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uguaauggca ggcacagguc u                                                 21

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
guaacaagcc agauuu                                                       16

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaucuggcu uguuacaggc a                                                 21

<210> SEQ ID NO 41
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uugcaccuuu cuaguu                                                       16

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aacuagaaag gugcaaacau g                                                 21

<210> SEQ ID NO 43
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gagugugacc aaaagu                                              16

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
acuuuugguc acacucucaa c                                        21

<210> SEQ ID NO 45
<211> LENGTH: 2358
<212> TYPE: DNA
<213> ORGANISM: Homo sapiens

<400> SEQUENCE: 45
aaactcacac aacaactctt ccccgctgag aggagacagc cagtgcgact ccaccctcca     60
gctcgacggc agccgccccg gccgacagcc ccgagacgac agcccggcgc gtccccggtcc   120 ccacctccga ccaccgccag cgctccaggc cccgccgctc cccgctcgcc gccaccgcgc   180
cctccgctcc gcccgcagtg ccaaccatga ccgccgccag tatgggcccc gtccgcgtcg   240
ccttcgtggt cctcctcgcc ctctgcagcc ggccggccgt cggccagaac tgcagcgggc   300
cgtgccggtg cccggacgag ccggcgccgc gctgcccggc gggcgtgagc ctcgtgctgg   360
acggctgcgg ctgctgccgc gtctgcgcca agcagctggg cgagctgtgc accgagcgcg   420 accctgcga cccgcacaag ggcctcttct gtgacttcgg ctccccggcc aaccgcaaga   480
tcggcgtgtg caccgccaaa gatggtgctc cctgcatctt cggtggtacg gtgtaccgca   540
gcggagagtc cttccagagc agctgcaagt accagtgcac gtgcctggac ggggcggtgg   600
gctgcatgcc cctgtgcagc atggacgttc gtctgcccag ccctgactgc cccttcccga   660
ggagggtcaa gctgcccggg aaatgctgcg aggagtgggt gtgtgacgag cccaaggacc   720
aaaccgtggt tgggcctgcc ctcgcggctt accgactgga agacacgttt ggcccagacc   780
caactatgat tagagccaac tgcctggtcc agaccacaga gtggagcgcc tgttccaaga   840
cctgtgggat gggcatctcc acccgggtta ccaatgacaa cgcctcctgc aggctagaga   900
agcagagccg cctgtgcatg gtcaggcctt gcgaagctga cctggaagag aacattaaga   960
agggcaaaaa gtgcatccgt actcccaaaa tctccaagcc tatcaagttt gagctttctg  1020
gctgcaccag catgaagaca taccgagcta aattctgtgg agtatgtacc gacggccgat  1080
gctgcacccc ccacagaacc accaccctgc cggtggagtt caagtgccct gacggcgagg  1140
tcatgaagaa gaacatgatg ttcatcaaga cctgtgcctg ccattacaac tgtcccggag  1200
acaatgacat ctttgaatcg ctgtactaca ggaagatgta cggagacatg gcatgaagcc  1260
agagagtgag agacattaac tcattagact ggaacttgaa ctgattcaca tctcattttt  1320
ccgtaaaaat gatttcagta gcacaagtta tttaaatctg tttttctaac tgggggaaaa  1380
gattcccacc caattcaaaa cattgtgcca tgtcaaacaa atagtctatc aaccccagac  1440
actggtttga agaatgttaa gacttgacag tggaactaca ttagtacaca gcaccagaat  1500
gtatattaag gtgtggcttt aggagcagtg ggagggtacc agcagaaagg ttagtatcat  1560
cagatagcat cttatacgag taatatgcct gctatttgaa gtgtaattga gaggaaaat  1620

-continued

```
tttagcgtgc tcactgacct gcctgtagcc ccagtgacag ctaggatgtg cattctccag    1680
ccatcaagag actgagtcaa gttgttcctt aagtcagaac agcagactca gctctgacat    1740
tctgattcga atgacactgt tcaggaatcg gaatcctgtc gattagactg gacagcttgt    1800
ggcaagtgaa tttgcctgta acaagccaga ttttttaaaa tttatattgt aaatattgtg    1860
tgtgtgtgtg tgtgtgtata tatatatata tgtacagtta tctaagttaa tttaaagttg    1920
tttgtgcctt tttatttttg tttttaatgc tttgatattt caatgttagc ctcaatttct    1980
gaacaccata ggtagaatgt aaagcttgtc tgatcgttca aagcatgaaa tggatactta    2040
tatggaaatt ctgctcagat agaatgacag tccgtcaaaa cagattgttt gcaaggggga    2100
ggcatcagtg tccttggcag gctgatttct aggtaggaaa tgtggtagcc tcacttttaa    2160
tgaacaaatg gcctttatta aaaactgagt gactctatat agctgatcag ttttttcacc    2220
tggaagcatt tgtttctact ttgatatgac tgttttttcgg acagtttatt tgttgagagt    2280
gtgaccaaaa gttacatgtt tgcacctttc tagttgaaaa taaagtgtat attttttcta    2340
taaaaaaaaa aaaaaaaa                                                  2358
```

<210> SEQ ID NO 46
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cauagguaga auguaa                                                         16

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuacauucua ccuauggugu u                                                   21

<210> SEQ ID NO 48
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uauagcugau caguuu                                                         16

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aaacugauca gcuauauaga g                                                   21

<210> SEQ ID NO 50
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ccagcaugaa gacaua                                                     16

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaugucuuca ugcuggugca g                                               21

<210> SEQ ID NO 52
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ccagaaugua uauuaa                                                     16

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuaauauaca uucuggugcu g                                               21

<210> SEQ ID NO 54
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
caaauggccu uuauua                                                     16

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uaauaaaggc cauuuguuca u                                               21

<210> SEQ ID NO 56

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gacauaccga gcuaaa                                                       16

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uuuagcucgg uaugucuuca u                                                 21

<210> SEQ ID NO 58
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ucaaguuguu ccuuaa                                                       16

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uuaaggaaca acuugacuca g                                                 21

<210> SEQ ID NO 60
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aagacauacc gagcua                                                       16

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uagcucggua ugucuucaug c                                                 21

<210> SEQ ID NO 62
<211> LENGTH: 16
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
accagcagaa agguua                                              16

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uaaccuuucu gcugguaccc u                                        21

<210> SEQ ID NO 64
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uaauugagaa ggaaaa                                              16

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uuuuccuucu caauuacacu u                                        21

<210> SEQ ID NO 66
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
accgcaagau cggcgu                                              16

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acgccgaucu ugcgguuggc c                                        21

<210> SEQ ID NO 68
<211> LENGTH: 16
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 68
ccaaccauga ccgccg                                                      16

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cggcggucau gguuggcacu g                                                21

<210> SEQ ID NO 70
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uggaguucaa gugccc                                                      16

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gggcacuuga acuccaccgg c                                                21

<210> SEQ ID NO 72
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
acccgcacaa gggccu                                                      16

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aggcccuugu gcggucgca g                                                 21

<210> SEQ ID NO 74
<211> LENGTH: 16
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 74
ugccccuucc cgagga                                                        16

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uccucgggaa ggggcaguca g                                                  21

<210> SEQ ID NO 76
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
acagcuagga ugugca                                                        16

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ugcacauccu agcugucacu g                                                  21

<210> SEQ ID NO 78
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ccaacuauga uuagag                                                        16

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cucuaaucau aguugggucu g                                                  21

<210> SEQ ID NO 80
<211> LENGTH: 16
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 80
ugaagacaua ccgagc                                                         16

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gcucgguaug ucuucaugcu g                                                   21

<210> SEQ ID NO 82
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
aggcugauuu cuaggu                                                         16

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
accuagaaau cagccugcca a                                                   21

<210> SEQ ID NO 84
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cucccaaaau cuccaa                                                         16

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uuggagauuu ugggaguacg g                                                   21

<210> SEQ ID NO 86
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 86
acuggaagac acguuu                                                        16

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aaacgugucu uccagucggu a                                                  21

<210> SEQ ID NO 88
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ggguuaccaa ugacaa                                                        16

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uugucauugg uaacccgggu g                                                  21

<210> SEQ ID NO 90
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
gaccuggaag agaaca                                                        16

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uguucucuuc caggucagcu u                                                  21

<210> SEQ ID NO 92
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ggaagagaac auuaag                                                              16

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
cuuaauguuc ucuuccaggt c                                                        21

<210> SEQ ID NO 94
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ccaagccuau caaguu                                                              16

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aacuugauag gcuuggagau u                                                        21

<210> SEQ ID NO 96
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
cauaccgagc uaaauu                                                              16

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
aauuuagcuc gguaugucuu c                                                        21

<210> SEQ ID NO 98
<211> LENGTH: 16
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 98
aaauucugug gaguau                                                         16

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
auacuccaca gaauuuagcu c                                                   21

<210> SEQ ID NO 100
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
cuggaagaga acauua                                                         16

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uaauguucuc uuccagguca g                                                   21

<210> SEQ ID NO 102
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uggaagagaa cauuaa                                                         16

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uuaauguucu cuuccagguc a                                                   21

<210> SEQ ID NO 104
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 104
uggaacuuga acugau                                                           16

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aucaguucaa guuccagucu a                                                     21

<210> SEQ ID NO 106
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uucuccagcc aucaag                                                           16

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
cuugauggcu ggagaaugca c                                                     21

<210> SEQ ID NO 108
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
caccauaggu agaaug                                                           16

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
cauucuaccu augguguuca g                                                     21

<210> SEQ ID NO 110
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 110
cguucaaagc augaaa                                                                  16

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uuucaugcuu ugaacgauca g                                                            21

<210> SEQ ID NO 112
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
guuuuucgga caguuu                                                                  16

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
aaacuguccg aaaaacaguc a                                                            21

<210> SEQ ID NO 114
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
aagauuccca cccaau                                                                  16

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
auugggnggg aaucuuuucc c                                                            21

<210> SEQ ID NO 116
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 116
ggcaugaagc cagaga                                              16

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ucucuggcuu caugccaugu c                                        21

<210> SEQ ID NO 118
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cucauuuuuc cguaaa                                              16

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuuacggaaa aaugagaugu g                                        21

<210> SEQ ID NO 120
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gucccggaga caauga                                              16

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
ucauugucuc cgggacaguu g                                        21

<210> SEQ ID NO 122
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
```
aucguucaaa gcauga                                              16

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ucaugcuuug aacgaucaga c                                        21

<210> SEQ ID NO 124
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ucuauauagc ugauca                                              16

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ugaucagcua uauagaguca c                                        21

<210> SEQ ID NO 126
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ccguccgcgu cgccuu                                              16

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
aaggcgacgc ggacggggcc c                                        21

<210> SEQ ID NO 128
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128

```
cagcugggcg agcugu                                                      16
```

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129

```
acagcucgcc cagcugcuug g                                                21
```

<210> SEQ ID NO 130
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130

```
gugcaccgcc aaagau                                                      16
```

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131

```
aucuuuggcg gtgcacacgc c                                                21
```

<210> SEQ ID NO 132
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132

```
gagcagcugc aaguac                                                      16
```

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133

```
guacuugcag cugcucugga a                                                21
```

<210> SEQ ID NO 134
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 134
ugauuagagc caacug                                                    16

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
caguuggcuc uaaucauagu u                                              21

<210> SEQ ID NO 136
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
agacauaccg agcuaa                                                    16

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uuagcucggu augucuucau g                                              21

<210> SEQ ID NO 138
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
acucauuaga cuggaa                                                    16

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uuccagucua augaguuaau g                                              21

<210> SEQ ID NO 140
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
```

-continued agauagcauc uuauac 16

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
guauaagaug cuaucugaug a 21

<210> SEQ ID NO 142
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
agagacugag ucaagu 16

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
acuugacuca gucucuugau g 21

<210> SEQ ID NO 144
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
aaugacaguc cgucaa 16

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uugacggacu gucauucuau c 21

<210> SEQ ID NO 146
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gccgcgucug cgccaa                                           16

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uggcgcagac gcggcagcag c                                     21

<210> SEQ ID NO 148
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ugugcagcau ggacgu                                           16

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
acguccaugc ugcacagggg c                                     21

<210> SEQ ID NO 150
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
cugugcagca uggacg                                           16

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
cguccaugcu gcacaggggc a                                     21

<210> SEQ ID NO 152
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
cccugacugc cccuuc                                           16

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gaaggggcag ucagggcugg g                                              21

<210> SEQ ID NO 154
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gcccugacug ccccuu                                                    16

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
aaggggcagu cagggcuggg c                                              21

<210> SEQ ID NO 156
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gugacgagcc caagga                                                    16

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uccuugggcu cgucacacac c                                              21

<210> SEQ ID NO 158
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ugugugacga gcccaa                                                    16

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uugggcucgu cacacaccca c                                           21

<210> SEQ ID NO 160
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
agugggugug ugacga                                                 16

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ucgucacaca cccacuccuc g                                           21

<210> SEQ ID NO 162
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
aggagugggu guguga                                                 16

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ucacacaccc acuccucgca g                                           21

<210> SEQ ID NO 164
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cgaggagugg gugugu                                                 16

```
<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
acacacccac uccucgcagc a                                              21

<210> SEQ ID NO 166
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ugcgaggagu gggugu                                                    16

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
acacccacuc cucgcagcau u                                              21

<210> SEQ ID NO 168
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
cagacccaac uaugau                                                    16

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aucauaguug ggucugggcc a                                              21

<210> SEQ ID NO 170
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ccagacccaa cuauga                                                    16

<210> SEQ ID NO 171
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ucauaguugg gucugggcca a                                              21

<210> SEQ ID NO 172
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
cccagaccca acuaug                                                    16

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cauaguuggg ucugggccaa a                                              21

<210> SEQ ID NO 174
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
gaguggagcg ccuguu                                                    16

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
aacaggcgcu ccacucugug g                                              21

<210> SEQ ID NO 176
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
guccagacca cagagu                                                    16

<210> SEQ ID NO 177
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
acucuguggu cuggaccagg c                                          21

<210> SEQ ID NO 178
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
ugguccagac cacaga                                                16

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
ucuguggucu ggaccaggca g                                          21

<210> SEQ ID NO 180
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ccugguccag accaca                                                16

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uguggucugg accaggcagu u                                          21

<210> SEQ ID NO 182
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
aacugccugg uccaga                                                16

<210> SEQ ID NO 183
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 183
ucuggaccag gcaguuggcu c        21

<210> SEQ ID NO 184
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gggaugggca ucucca        16

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uggagaugcc caucccacag g        21

<210> SEQ ID NO 186
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186 uguggaugg gcaucu        16

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
agaugcccau cccacagguc u        21

<210> SEQ ID NO 188
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188 cuguggaug ggcauc        16

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gaugcccauc ccacaggucu u                                              21

<210> SEQ ID NO 190
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
agggcaaaaa gugcau                                                    16

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
augcacuuuu ugcccuucuu a                                              21

<210> SEQ ID NO 192
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
uaagaagggc aaaaag                                                    16

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
cuuuuugccc uucuuaaugu u                                              21

<210> SEQ ID NO 194
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cuuucuggcu gcacca                                                    16

<210> SEQ ID NO 195
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 195
uggugcagcc agaaagcuca a                                              21

<210> SEQ ID NO 196
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gagcuuucug gcugca                                                    16

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ugcagccaga aagcucaaac u                                              21

<210> SEQ ID NO 198
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
cugccauuac aacugu                                                    16

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
acaguuguaa uggcaggcac a                                              21

<210> SEQ ID NO 200
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gccugccauu acaacu                                                    16

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 201
aguuguaaug gcaggcacag g     21

<210> SEQ ID NO 202
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ugccugccau uacaac     16

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
guuguaaugg caggcacagg u     21

<210> SEQ ID NO 204
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
gugccugcca uuacaa     16

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uuguaauggc aggcacaggu c     21

<210> SEQ ID NO 206
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ugugccugcc auuaca     16

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uguaauggca ggcacagguc u                                              21

<210> SEQ ID NO 208
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
ccugugccug ccauua                                                    16

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uaauggcagg cacaggucuu g                                              21

<210> SEQ ID NO 210
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
accugugccu gccauu                                                    16

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
aauggcaggc acaggucuug a                                              21

<210> SEQ ID NO 212
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gaccugugcc ugccau                                                    16

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 213
auggcaggca caggucuuga u                                              21

<210> SEQ ID NO 214
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
guucaucaag accugu                                                    16

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
acaggucuug augaacauca u                                              21

<210> SEQ ID NO 216
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
agauguacgg agacau                                                    16

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
augucuccgu acaucuuccu g                                              21

<210> SEQ ID NO 218
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ggaagaugua cggaga                                                    16

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
```
ucuccguaca ucuuccugua g                                                     21

<210> SEQ ID NO 220
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cuacaggaag auguac                                                           16

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
guacaucuuc cuguaguaca g                                                     21

<210> SEQ ID NO 222
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
acagcuugug gcaagu                                                           16

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
acuugccaca agcuguccag u                                                     21

<210> SEQ ID NO 224
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
gacagcuugu ggcaag                                                           16

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cuugccacaa gcuguccagu c                                              21

<210> SEQ ID NO 226
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ggacagcuug uggcaa                                                    16

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uugccacaag cuguccaguc u                                              21

<210> SEQ ID NO 228
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aacaagccag auuuuu                                                    16

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
aaaaaucugg cuuguuacag g                                              21

<210> SEQ ID NO 230
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
guaacaagcc agauuu                                                    16

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
aaaucuggcu uguuacaggc a                                              21

<210> SEQ ID NO 232
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
cuguaacaag ccagau                                                    16

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
aucuggcuug uuacaggcaa a                                              21

<210> SEQ ID NO 234
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
ucuaaguuaa uuuaaa                                                    16

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
uuuaaauuaa cuuagauaac u                                              21

<210> SEQ ID NO 236
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
caccuuucua guugaa                                                    16

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
uucaacuaga aaggugcaaa c                                              21

```
<210> SEQ ID NO 238
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uugcaccuuu cuaguu                                                        16

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
aacuagaaag gugcaaacau g                                                  21

<210> SEQ ID NO 240
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
cauguuugca ccuuuc                                                        16

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gaaaggugca aacauguaac u                                                  21

<210> SEQ ID NO 242
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gagugugacc aaaagu                                                        16

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
acuuuggguc acacucucaa c                                                  21
```

-continued

<210> SEQ ID NO 244
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
agagugugac caaaag                                                         16

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
gagtcaacgg atttggtcgt                                                     20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gacaagcttc ccgttctcag                                                     20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
caagggcctc ttctgtgact                                                     20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
acgtgcactg gtacttgcag                                                     20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
tgcagtggga attgtgacct                                                     20

<210> SEQ ID NO 250

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
ggaatcggac cttaccctga                                              20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
tcatcgtggc ttctctggtc                                              20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gaccgttgag tccgtctttg                                              20

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
acgtaagcac tggtggacag a                                            21

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gagggccata gctgaactga                                              20

<210> SEQ ID NO 255
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
gtgtagcaca acttccaatt acgaa                                        25

<210> SEQ ID NO 256
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ggaatttccg cctcgagtct                                                   20

<210> SEQ ID NO 257
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
cuuaccgacu ggaaga                                                       16

<210> SEQ ID NO 258
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
ucuuccaguc gguaagccgc g                                                 21

<210> SEQ ID NO 259
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
ucuuccaguc gguaagccgc gag                                               23

<210> SEQ ID NO 260
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
ucuuccaguc gguaagccgc gaggg                                             25

<210> SEQ ID NO 261
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
ucuuccaguc gguaagccgc gagggca                                           27

<210> SEQ ID NO 262
<211> LENGTH: 29
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 262
ucuuccaguc gguaagccgc gagggcagg                                              29

<210> SEQ ID NO 263
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ucuuccaguc gguaagccgc gagggcaggc c                                           31
```